(12) United States Patent
Bezwada

(10) Patent No.: US 8,901,347 B1
(45) Date of Patent: *Dec. 2, 2014

(54) ABSORBABLE POLYURETHANES AND METHODS OF USE THEREOF

(75) Inventor: Rao S. Bezwada, Whitehouse Station, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 329 days.

This patent is subject to a terminal disclaimer.

(21) Appl. No.: 13/275,902

(22) Filed: Oct. 18, 2011

Related U.S. Application Data

(60) Provisional application No. 61/422,447, filed on Dec. 13, 2010.

(51) Int. Cl.
- *A61K 47/16* (2006.01)
- *C07C 265/14* (2006.01)
- *C07C 265/12* (2006.01)
- *C07C 211/46* (2006.01)
- *A61K 47/14* (2006.01)

(52) U.S. Cl.
CPC .............. *C07C 265/12* (2013.01); *C07C 211/46* (2013.01); *A61K 47/14* (2013.01); *C07C 265/14* (2013.01); *A61K 47/16* (2013.01)
USPC ............. 560/359; 560/330; 528/44; 528/331; 514/785; 514/788

(58) Field of Classification Search
CPC ...... A61K 47/14; A61K 47/16; C07C 265/12; C07C 265/14
USPC ............. 560/330, 359; 528/44, 331; 514/785, 514/788
See application file for complete search history.

(56) References Cited

U.S. PATENT DOCUMENTS

| | | | |
|---|---|---|---|
| 3,492,332 A | 1/1970 | Ulrich et al. | |
| 4,740,534 A | 4/1988 | Matsuda et al. | |
| 4,829,099 A | 5/1989 | Fuller et al. | |
| 4,994,542 A | 2/1991 | Matsuda et al. | |
| 5,173,301 A | 12/1992 | Itoh et al. | |
| 5,552,507 A | 9/1996 | Wamprecht et al. | |
| 6,894,140 B2 | 5/2005 | Roby | |
| 7,772,352 B2 | 8/2010 | Bezwada | |
| 2006/0288547 A1 | 12/2006 | Jackson | |
| 2009/0082540 A1 | 3/2009 | Bezwada | |
| 2009/0292029 A1 | 11/2009 | Bezwada | |
| 2010/0260702 A1 | 10/2010 | Bezwada | |

FOREIGN PATENT DOCUMENTS

| | | |
|---|---|---|
| EP | 0295055 A2 | 12/1988 |
| EP | 1937182 B1 | 12/2010 |
| EP | 2298235 A1 | 3/2011 |
| WO | 07030464 A2 | 3/2007 |

OTHER PUBLICATIONS

Bezwada et al., "Poly(p-dioxanone) and its copolymers," Handbook of Biodegradable Polymers, pp. 29-30.
Bezwada, Rao. S., "Absorbable Polyurethanes," Technical White Paper (Jul. 2008).
Bezwada, Rao S., "Synthetic Absorbable Polyesters," Technical White Paper (Jul. 2008).
Bruin et al., "Design and synthesis of biodegradable poly(ester-urethane) elastomer networks composed of non-toxic building blocks," Makromol. Chem., Rapid Commun. (1988), vol. 9, pp. 589-894.
Extended Search Report for EP 06814181.1 issued Jun. 17, 2009.

*Primary Examiner* — Barbara Badio
*Assistant Examiner* — Sara E Townsley
(74) *Attorney, Agent, or Firm* — Fox Rothschild LLP; Peter J. Butch, III; Robert N. Henrie, II

(57) ABSTRACT

Disclosed are novel bioabsorbable and biodegradable monomer compounds, bioabsorbable and biodegradable polymers therefrom, and methods of making such monomers and polymers, which are useful in pharmaceutical delivery systems, tissue engineering applications, tissue adhesives products, implantable medical devices, foams and reticulated foams for wound healing and drug delivery, bone hemostats and bone void fillers, adhesion prevention barriers, meshes, filters, stents, medical device coatings, pharmaceutical drug formulations, consumer product and cosmetic and pharmaceutical packaging, apparel, infusion devices, blood collection tubes and devices, other medical tubes, skin care products, and transdermal drug delivery materials.

20 Claims, No Drawings

ABSORBABLE POLYURETHANES AND METHODS OF USE THEREOF

CROSS-REFERENCE TO RELATED APPLICATIONS

The present application claims the benefit of priority under 35 U.S.C. §119(e) of Provisional Application Ser. No. 61/422,447, filed on Dec. 13, 2010, the entire disclosure of which is incorporated by reference herein.

FIELD OF THE INVENTION

The present invention relates to the discovery of a new class of bioabsorbable and biodegradable polyurethanes, polyester urethanes and polyamides, their respective monomeric units and intermediates for the preparation thereof. The resultant absorbable polymers are useful for drug delivery matrices, therapeutic compositions, tissue engineering, tissue adhesives, adhesion prevention, and other implantable medical devices. Further, the absorbable polymers of the present invention provide a controllable degradation profile.

BACKGROUND OF THE INVENTION

Biodegradable polymers have become increasingly important for a variety of biomedical applications including tissue engineering scaffolds, surgical adhesives, sutures, medical device coatings and drug delivery matrices, etc.

Isocyanate-based adhesive/sealant compositions are known. For example, U.S. Pat. Nos. 6,894,140; 5,173,301; 4,994,542; and 4,740,534, provide disclosure of such compositions, the disclosures of all of which are incorporated herein by reference in their entirety.

However, the prior art compositions suffer from a number of shortcomings including a slow rate of degradation, and potential toxicity problems due to their reduced degradability.

BRIEF SUMMARY OF THE INVENTION

The present invention overcomes the problems that are characteristic of the prior art polymeric moieties. It is the object of the present invention to provide novel materials and methods of making such materials which would ultimately be useful for drug delivery, tissue engineering, tissue adhesives, adhesion prevention and other implantable medical devices.

In one aspect of the present invention, novel aromatic amine-containing monomeric units are disclosed. Another embodiment is directed to bioabsorbable and biodegradable polyamides containing repeating units, including the presently disclosed novel aromatic amine-containing monomeric units. In another embodiment of the invention, novel methods for preparing such biodegradable and biocompatible polyamides, their respective prepolymers, intermediates, and compositions thereof are disclosed. In yet another embodiment of the present invention, novel biodegradable and biocompatible polymers having a controllable degradation profile are disclosed, for medicinal and therapeutic uses, such as tissue engineering.

In another aspect of the present invention, novel biodegradable and biocompatible aromatic diisocyanates are disclosed. In another embodiment bioabsorbable and biodegradable polyurethanes and polyurethane esters containing repeating units having the structure of the disclosed aromatic diisocyanate-containing monomeric units are disclosed. In another embodiment of the present invention, novel methods for preparing such biodegradable and biocompatible polyurethanes and polyurethane esters, their respective prepolymers, intermediates, and compositions thereof are disclosed. In another embodiment of the present invention, novel biodegradable and biocompatible polymers are disclosed, for medicinal and therapeutic uses, for example, without limitation, in such fields as tissue engineering, reticulated foams for wound healing and drug deliver, bone hemostats and bone fillers.

In a further aspect of the present invention, novel biodegradable and biocompatible aliphatic and cyclic aliphatic diisocyanates are disclosed. Another embodiment is directed to bioabsorbable and biodegradable polyurethane and polyurethane esters containing repeating units having the structure of the disclosed aliphatic and cyclic aliphatic diisocyanate-containing monomeric units. In another embodiment of the present invention, novel methods for preparing such biodegradable and biocompatible aliphatic polyurethanes and polyurethane esters, their respective prepolymers, intermediates, and compositions thereof are disclosed. In another embodiment of the present invention, the novel biodegradable and biocompatible polymers are directed to medicinal and therapeutic uses, including but not limited to tissue engineering, reticulated foams for wound healing and drug delivery, bone hemostats and bone fillers.

In another embodiment, the present invention is directed to the application of novel hydrolysable isocyanates, amines, biodegradable and biocompatible polyurethanes and polyamides described in the present patent application, optionally in combination with those described in patents/patent publications U.S. Pat. No. 7,772,352, US 2010/0260702 A1, US 2009/0292029 A1, US 2009/0082540, US 2006/0288547 A1, EP 1937182 B1, EP 2298235 A1, EP 1937182 A4, EP 1937182 A2, and WO 2007030464 A2, all of which have been assigned to Bezwada Biomedical, and U.S. Pat. No. 4,829,099 assigned to Fuller, et al., for use in medicinal, medical device, therapeutic, consumer product and cosmetic applications including but not limited to tissue engineering, foams (including but not limited to reticulated foams, lyophilized foams and regular foams) for wound healing and drug delivery, bone hemostats and bone fillers, tissue adhesive and sealants, adhesion prevention barriers, meshes, filters, bone void fillers, controlled drug delivery, stents, medical device coatings, pharmaceutical drug formulations, medical device, cosmetic and pharmaceutical packaging, apparels, infusion devices, blood collection tubes and devices, tubes, skin care and transdermal drug delivery. The entire disclosures of all of the above-cited patents and patent publications are incorporated by reference herein.

In another embodiment, the present invention is directed to absorbable polyurethane foams with open and closed cell structures, including but not limited to reticulated foams, foams with vertical channels, architecturally gradient foams, trans-compositional foams and trans-structural foams and the process of preparing these absorbable foams using the novel hydrolysable isocyanates, amines, biodegradable and biocompatible polyurethanes described in the present patent application, optionally in combination with those described in patents/patent publications U.S. Pat. No. 7,772,352, US 2010/0260702 A1, US 2009/0292029 A1, US 2009/0082540, US 2006/0288547 A1, EP 1937182 B1, EP 2298235 A1, EP 1937182 A4, EP 1937182 A2, and WO 2007030464 A2, all of which are assigned to Bezwada Biomedical, and U.S. Pat. No. 4,829,099, assigned to Fuller, et al., via lyophilization wherein the absorbable polyurethane polymers and/or blends thereof are dissolved in a suitable solvent such as, without limitation, dioxane, N-methylpyrrolidone, dichloromethane and/or mixtures thereof, to form a homogeneous solution which is subjected to a lyophilization process comprising a solution of a bioabsorbable elastomer in a solvent which is substantially, but not necessarily completely, solidified, then the solvent is removed from that which is lyophilized under reduced pressure to form a foam. The entire disclosures of all of the above-cited patents and patent publications are incorporated by reference herein.

In another embodiment, isocyanates of the present invention provide a true reticulated, flexible, resilient, bioabsorbable elastomeric matrix, suitable for implantation and having sufficient porosity to encourage cellular ingrowth and proliferation in vivo. The present invention also provides a polymerization process for preparing an absorbable reticulated elastomeric matrix, the process comprising the steps of:

(1) admixing
  a) a polyol component,
  b) an isocyanate component,
  c) a blowing agent,
  d) optionally, a crosslinking agent,
  e) optionally, a chain extender,
  f) optionally, one or more catalysts,
  g) optionally, one or more cell openers,
  h) optionally, a surfactant, and
  i) optionally, a viscosity modifier;
to provide a crosslinked elastomeric matrix, and (2) reticulating the elastomeric matrix by a reticulation process to provide the reticulated elastomeric matrix.

The ingredients are present in quantities and the elastomeric matrix is prepared under conditions so as to:

(i) provide a crosslinked resiliently-compressible bioabsorbable elastomeric matrix, (ii) control formation of biologically undesirable residues, and (iii) reticulate the foam by a reticulation process, to provide the reticulated elastomeric matrix.

In another embodiment, the invention is directed to a lyophilization process for preparing a reticulated elastomeric matrix comprising lyophilizing a flowable polymeric material. In another embodiment, the polymeric material comprises a solution of a solvent-soluble bioabsorbable elastomer in a solvent. In another embodiment, the flowable polymeric material is subjected to a lyophilization process comprising solidifying the flowable polymeric material to form a solid, e.g., by cooling a solution, then removing the non-polymeric material, e.g., by evaporating the solvent from the solid under reduced pressure, to provide an at least partially reticulated elastomeric matrix. In another embodiment, a solution of a bioabsorbable elastomer in a solvent is substantially, but not necessarily completely, solidified, then the solvent is evaporated from that material to provide an at least partially reticulated elastomeric matrix. In another embodiment, the temperature to which the solution is cooled is below the freezing temperature of the solution. In another embodiment, the temperature to which the solution is cooled is above the apparent glass transition temperature of the solid and below the freezing temperature of the solution.

In another embodiment, the invention is directed to a lyophilization process for producing an elastomeric matrix having a reticulated structure, the process comprising the steps of:

a) forming a solution comprising a solvent-soluble bioabsorbable elastomer in a solvent;
b) at least partially solidifying the solution to form a solid, optionally by cooling the solution; and
c) removing the non-polymeric material, optionally by evaporating the solvent from the solid under reduced pressure, to provide an at least partially reticulated elastomeric matrix comprising the elastomer.

Another embodiment of the invention is directed to a process for preparing a reticulated composite elastomeric implantable device for implantation into a patient, the process comprising surface coating or endoporously coating a bioabsorbable reticulated elastomeric matrix with a coating material selected to encourage cellular ingrowth and proliferation. The coating material can, for example, comprise a foamed coating of bioabsorbable polyurethane, optionally, collagen, fibronectin, elastin, hyaluronic acid or a mixture thereof. Alternatively, the coating comprises bioabsorbable polyurethane and an inorganic component.

Another object of the present invention is to provide novel safe, biocompatible and bioabsorbable aromatic isocyanate-based adhesives. More particularly, such adhesives are metabolically-acceptable surgical adhesives and have controllable degradation profiles. In yet another aspect of the present invention, methods for closing wounds in living tissue by use of novel, metabolically-acceptable surgical adhesives having low toxicity are disclosed.

DETAILED DESCRIPTION OF PREFERRED EMBODIMENTS

The present invention provides new classes of amines, isocyanates and bioabsorbable urethanes, aromatic amides and esterurethane compounds and their respective polymerized moieties, polyurethanes, polyamides and polyesterurethanes. The resultant absorbable polymers are useful for drug delivery as matrices, fillers, coatings, etc; tissue engineering complexes and scaffoldings; tissue adhesives, foams, including reticulated foams, adhesion prevention matrices and other implantable medical devices. In addition these absorbable polymers are characterized by having a controllable degradation profile.

The term "bioabsorbable" is defined as readily reacting or enzymatically degrading upon exposure to bodily tissue for a relatively short period of time, thus providing a significant loss of the original material in that short time period. Complete bioabsorption should take place within twelve months, although preferably within three to nine months. Preferably, bioabsorption is complete within nine months, and most preferably within six months. Therefore, the polymers of the invention can be fabricated into medical and surgical devices, foams, bioadhesives, coatings, etc., which are useful for a vast array of applications requiring complete absorption within the relatively short time periods as defined above.

The biological properties of the bioabsorbable polymers of this invention used to form the device or part thereof, as measured by its absorption rate and its breaking strength retention in vivo (BSR), can be adjusted to suit the needs of the particular application for which the fabricated medical device or component is intended. Those of ordinary skill in the art can appreciate that modifications in the ratios of the specific components will affect the degradation rate.

For purposes of defining the scope of this invention, the term "elastomer" is defined as a material which at room temperature can be stretched repeatedly to at least twice its original length and, upon immediate release of the stress, will return with force to its approximate original length.

The term "prepolymer" is defined as a low molecular weight polymer usually an intermediate between that of the monomer and the final polymer that is capable of further polymerization.

The term "monomeric unit" is defined as a small molecule that can chemically react with other monomers to form a polymer. The term "polymer" is defined as a molecule that is formed by joining repeating monomeric units. The polymers of the present invention can be, without limitation, linear, branced, star or comb polymers.

In the preferred embodiments of this invention, the polymer from which a medical device or a component of the device is formed exhibits a percent elongation greater than about 200, preferably greater than about 500. It will also exhibit a modulus (Young's Modulus) of less than about 40,000 psi, preferably less than about 20,000 psi. These properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch Generally the functionality of the aromatic monomers is selected from amine- and/or carboxylic acid-containing phenols, such as amino phenols and amino salicylic acids, and from amino benzoic acids, as summarized below. Glycolic acid is used as a functionalization moiety for purposes of illustration.

Precursors of the Compounds and Monomeric Units

Glycolic acid and lactic acid are known as alpha-hydroxy acids (AHAs) and are present in fruits and other foods. The chemical formula of glycolic acid is $HOCH_2COOH$. This compound is biodegradable. When glycolic acid is heated it readily loses water by self-esterification to form polyglycolic acid. Glycolic acid can function as both an acid and an alcohol. This dual functionality leads to a variety of chemical reactions and valuable physical properties. Many surgical devices are made from polyglycolic acid. The process of attaching a glycolic acid moiety to a phenolic compound is defined as glycolation.

Lactic acid is a fermentation product of lactose. It is present in sour milk, koumiss, leban, yogurt, and cottage cheese. Lactic acid is also produced in the muscles during intense activity. Many surgical and orthopedic devices are made from polylactic acid. The esters of lactic acid are useful as emulsifying agents in baking foods; examples include stearoyl-2-lactylate, glyceryl lactostearate, and glyceryl lactopalmitate. The process of attaching a lactic acid moiety to a phenolic compound is defined as lactolation.

Epsilon-caprolactone is a reactive cyclic monomer, and the polymers derived therefrom are useful for tailoring specialty polyols and hydroxy-functional polymer resins with enhanced flexibility. The monomer polymerizes under mild conditions to give low viscosity products superior to conventional aliphatic polyesters. Copolymers of caprolactone with glycolide and lactide exhibit unique physical and biological properties as well as different hydrolysis profiles based on the composition of the monomers. The process of attaching an open chain ε-caprolactone moiety to a phenolic compound is defined as caprolation.

p-Dioxanone (1,4-dioxan-2-one) is a cyclic monomer, and polymers are made therefrom via ring opening polymerization. Polyesters derived from this monomer are used in making absorbable surgical devices with a longer absorption profile (slower hydrolysis) compared to polyglycolic acid. The absorbable surgical devices made from 1,4-dioxan-2-one have proved to be biologically safe, and biocompatible. The process of attaching an open chain p-dioxanone moiety to a phenolic compound is defined as dioxonation.

Many examples of the phenolic amino acids reacted with the above functionalization moieties have been shown to be safe and biocompatible. Embodiments of the new functionalized phenolics have controllable hydrolysis profiles, improved bioavailability, improved efficacy and enhanced functionality. The disclosed difunctional compounds can readily polymerize into biodegradable polyesters, polyester amides, polyurethanes, polydiamides, and polyanhydrides, which are useful for many applications, including biomedical applications, foodstuffs, nutritional supplements, cosmetics, medicaments, coatings and others readily apparent to one skilled in the art.

Monomeric Units/Repeating Compounds

At least one aspect of the present invention focuses on novel compounds and monomeric units that can be used to form the backbone of a polymer. Accordingly, one aspect of the present invention is directed to compounds comprising at least one unit selected from the group consisting of formulas (1)-(15):

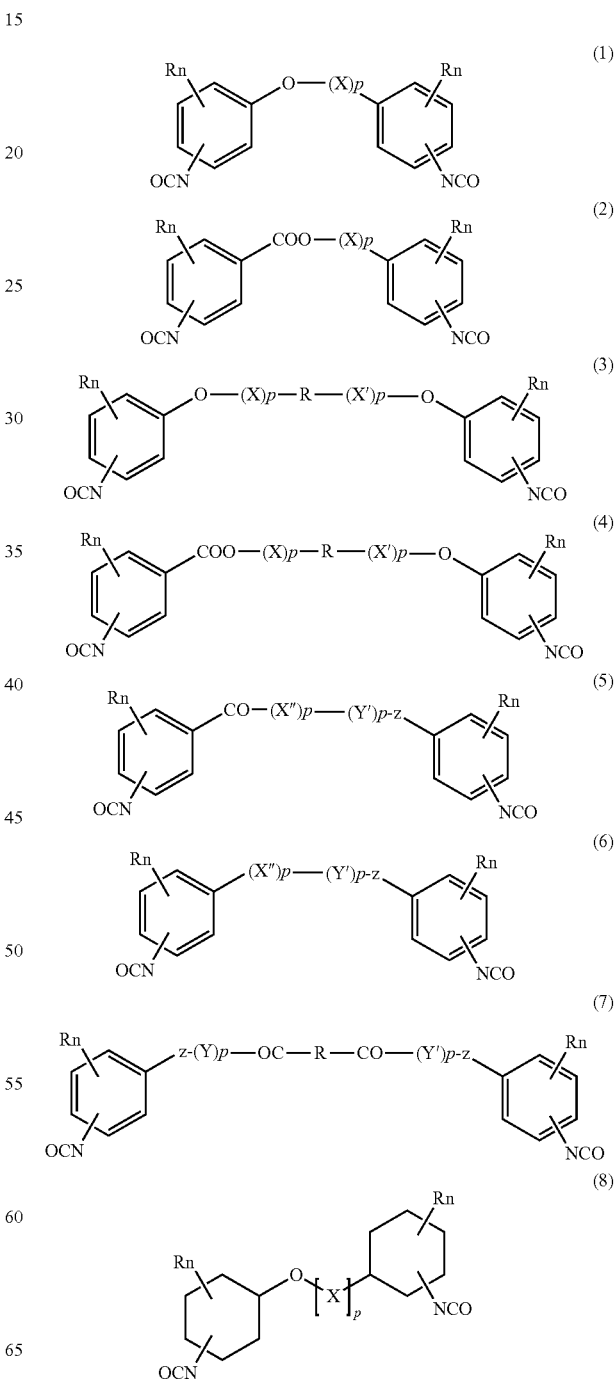

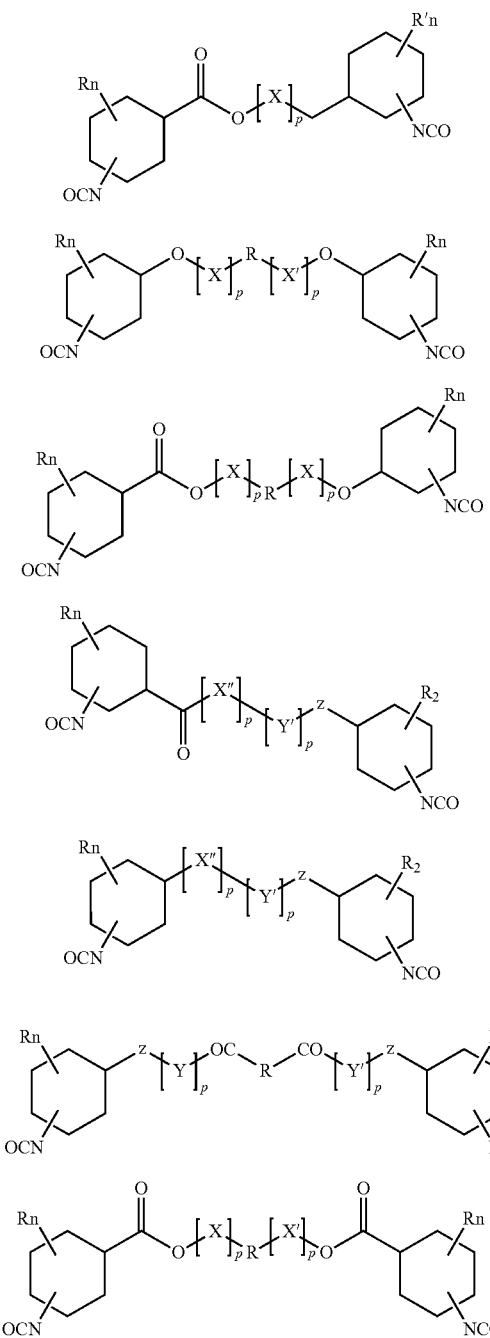

wherein each X represents a member independently selected from the group consisting of:
—CH$_2$COO— (glycolic acid moiety);
—CH(CH$_3$)COO— (lactic acid moiety);
—CH$_2$CH$_2$OCH$_2$COO— (dioxanone moiety);
—CH$_2$CH$_2$CH$_2$CH$_2$CH$_2$COO— (caprolactone moiety);
—(CH$_2$)$_y$COO— where y is one of the numbers 2, 3, 4 and 6-24 inclusive; and
—(CH$_2$CH$_2$O)$_z$·CH$_2$COO— where z' is an integer between 2 and 24, inclusive;
each X' represents a member independently selected from the group consisting of:
—OOCCH$_2$— (glycolic acid moiety);
—OOC(CH$_3$)CH— (lactic acid moiety);
—OOCCH$_2$OCH$_2$CH$_2$— (dioxanone moiety);
—OOCCH$_2$CH$_2$CH$_2$CH$_2$— (caprolactone moiety);
—OOC(CH$_2$)$_y$— where y is one of the numbers 2, 3, 4 and 6-24 inclusive; and
—OOCCH$_2$(OCH$_2$CH$_2$)z'- where z' is an integer between 2 and 24, inclusive;
each X" represents a member independently selected from the group consisting of:
—OCH$_2$CO— (glycolic acid moiety);
—OCH(CH$_3$)CO— (lactic acid moiety);
—OCH$_2$CH$_2$OCH$_2$CO— (dioxanone moiety);
—OCH$_2$CH$_2$CH$_2$CH$_2$CH$_2$CO— (caprolactone moiety);
—O(CH$_2$)$_y$CO— where y is one of the numbers 2, 3, 4 and 6-24 inclusive; and
—O(CH$_2$CH$_2$O)$_z$·'CH$_2$CO— where z' is an integer between 2 and 24, inclusive;
each Y represents a member independently selected from the group consisting of:
—COCH$_2$O— (glycolic ester moiety);
—COCH(CH$_3$)O— (lactic ester moiety);
—COCH$_2$OCH$_2$CH$_2$O— (dioxanone ester moiety);
—COCH$_2$CH$_2$CH$_2$CH$_2$CH$_2$O— (caprolactone ester moiety);
—CO(CH$_2$)$_m$O— where m is an integer between 2-4 and 6-24 inclusive; and
—COCH$_2$—O—(CH$_2$CH$_2$O)$_n$— where n is an integer between 2 and 24, inclusive;
each Y' represents a member independently selected from the group consisting of:
—OCH$_2$OC— (glycolic ester moiety);
—O(CH$_3$)CHOC— (lactic ester moiety);
—OCH$_2$CH$_2$OCH$_2$OC— (dioxanone ester moiety);
—OCH$_2$CH$_2$CH$_2$CH$_2$CH$_2$OC— (caprolactone ester moiety);
—O(CH$_2$)$_m$OC— where m is an integer between 2-4 and 6-24 inclusive; and
—(OCH$_2$CH$_2$)$_n$OCH$_2$OC— where n is an integer between 2 and 24 inclusive;
wherein Z is —O— or —S— or —NH—;
wherein R is an alkylene, alkenylene or alkynylene group which may be straight-chained or branched, and can optionally contain one or more oxygen atoms, sulfur atoms, ester groups, aromatic groups or halogen atoms. The alkylene, alkenylene or alkynylene group may also optionally be cyclic, represented by 1,4-cyclohexylidine or cyclohexane-1,4-methylene (—CH$_2$-c-C$_6$H$_{10}$—CH$_2$—), or the corresponding 1,2- or 1,3-isomers, for example, and optionally containing the above groups. Further, R may be phenylene or 1,4-xylylene (—CH$_2$—C$_6$H$_4$—CH$_2$—), or the corresponding 1,2- or 1,3-isomers, for example, optionally containing the above groups. R can also be an organic moiety derived from alkyl, benzyl, ethylene glycol, organic ether, carboxylic acid, dicarboxylic acid, or substituted or thio derivatives thereof, carrying one, two or three free valences in the form of mono-, di- or tri-valent radicals, including but not limited to methylene (—CH$_2$—), ethylene (—CH2CH2-), propylene (—CH2CH2CH2-), vinylene (—CH═CH—), propenylene (—CH═CHCH2-), and the like. In yet another embodiment, R is derived from a polyol, alkylene glycol, ethylene glycol, diethylene glycol, triethylene glycol, polyethylene glycol (polyethyl ether), diethyl ether, or optionally substituted analogs thereof. In yet another embodiment, R is a group derived from a diacid, including but not limited to succinic acid, adipic acid, malonic acid, diglycolic acid, or optionally substituted derivatives thereof. In still another embodiment R may be a bioabsorbable, biodegradable, and/or di-, tri- or multi-valant radical containing at least one oxygen, sulfur or halogen atom; where the R-groups are optionally substituted with alkyl, alkoxy and/or halogen.

Further, the aromatic substituents, Rn, represent one or more moieties selected from the group consisting of H, alkoxy, phenoxy, benzyloxy, formyl (—CHO), halogen, carboxylic acid and —NO$_2$, which are attached directly to an aromatic ring, or indirectly via an alkylene chain to form a substituted aromatic moiety. Preferably the alkylene chain contains 1-24 carbon atoms, more preferably 1-12 carbon atoms, still more preferably 1-6 carbon atoms, and most preferably 1-3 carbon atoms. The alkylene chain can be linear or branched. The substituents Rn can be selected such that the precursors are derived from amine- and/or carboxylic acid-containing phenols, including but not limited to amino phenols (ortho-, meta- or para-) and amino salicylic acids (ortho-, meta- or para-), and can also be derived from amino benzoic acids(ortho-, meta- or para-).

A further aspect of the invention is directed to monomers wherein the isocyanate groups are replaced with isothiocyanates; and polymers produced therefrom. Specifically, this aspect of the invention is directed to isothiocyanate analogs of (1)-(15), above.

In one aspect of the present invention, novel biodegradable and biocompatible aliphatic and cyclic aliphatic diisocyanate-based monomers are disclosed. Preferred cyclic aliphatic diisocyanate-based monomers are the cyclohexane-containing compounds (8)-(15), which are related to their aromatic counterparts (1)-(7) formally by reduction of the benzene rings to cyclohexane rings. The polymers prepared from such saturated monomers have beneficially reduced color, improved transparency and are non-yellowing.

In a more preferred embodiment, in the structures (1)-(15), X is selected from the group consisting of:
—CH$_2$COO— (glycolic acid moiety);
—CH(CH$_3$)COO— (lactic acid moiety);
—CH$_2$CH$_2$OCH$_2$COO— (dioxanone moiety);
—CH$_2$CH$_2$CH$_2$CH$_2$CH$_2$COO— (caprolactone moiety);
and mixtures thereof;
X' is selected from the group consisting of:
—OOCCH$_2$— (glycolic acid moiety);
—OOC(CH$_3$)CH— (lactic acid moiety);
—OOCCH$_2$OCH$_2$CH$_2$— (dioxanone moiety); and
—OOCCH$_2$CH$_2$CH$_2$CH$_2$CH$_2$— (caprolactone moiety);
X" is selected from the group consisting of:
—OCH$_2$CO— (glycolic acid moiety);
—OCH(CH$_3$)CO— (lactic acid moiety);
—OCH$_2$CH$_2$OCH$_2$CO— (dioxanone moiety); and
—OCH$_2$CH$_2$CH$_2$CH$_2$CH$_2$CO— (caprolactone moiety);
Y is selected from the group consisting of:
—COCH$_2$O— (glycolic ester moiety);
—COCH(CH$_3$)O— (lactic ester moiety);
—COCH$_2$OCH$_2$CH$_2$O— (dioxanone ester moiety); and
—COCH$_2$CH$_2$CH$_2$CH$_2$CH$_2$O— (caprolactone ester moiety);
and
Y' is selected from the group consisting of:
—OCH$_2$CO— (glycolic ester moiety);
—O(CH$_3$)CHCO— (lactic ester moiety);
—OCH$_2$CH$_2$OCH$_2$CO— (dioxanone ester moiety); and
—OCH$_2$CH$_2$CH$_2$CH$_2$CH$_2$CO— (caprolactone ester moiety);
wherein each R is a straight-chained, branched or cyclic alkylene group containing 1-24 carbon atoms, optionally containing one or more oxygen atoms, sulfur atoms, ester groups, halogen atoms, or aromatic groups.
each p is independently an integer between 0 and 4, inclusive;
Z is O or S or NH;
and
Rn represents one or more members selected from the group consisting of H, alkoxy, benzyloxy, aldehyde, halogen, carboxylic acid and —NO$_2$, and Rn is attached directly to the aromatic rings or attached through an alkylene chain.

Another aspect of the present invention focus on absorbable polyurethanes derived from at least one unit selected from the group consisting of formulas (1)-(15).

Another aspect of the present invention comprises a tissue adhesive composition comprising at least one monomer selected from the group consisting of formulas (1)-(15).

Another aspect of the present invention is directed to the preparation absorbable polyamide, polyester amides and polyureas containing compounds having at least one unit selected from the group consisting of formulas (16)-(30).

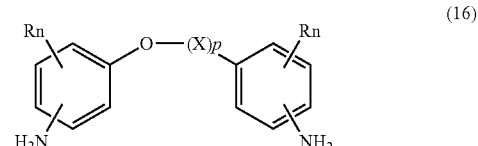

(16)

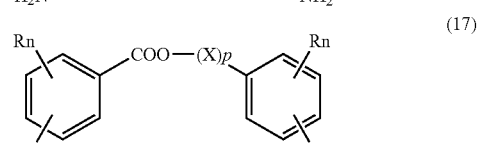

(17)

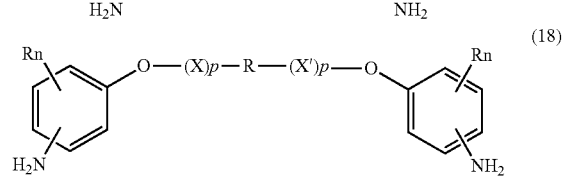

(18)

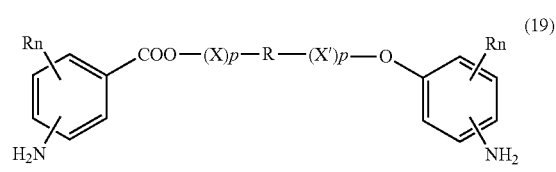

(19)

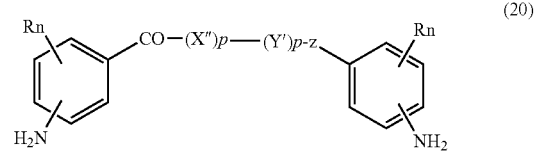

(20)

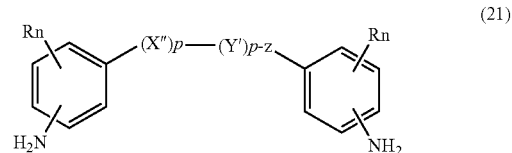

(21)

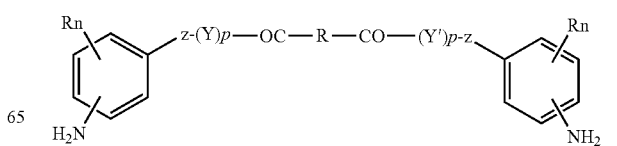

(22)

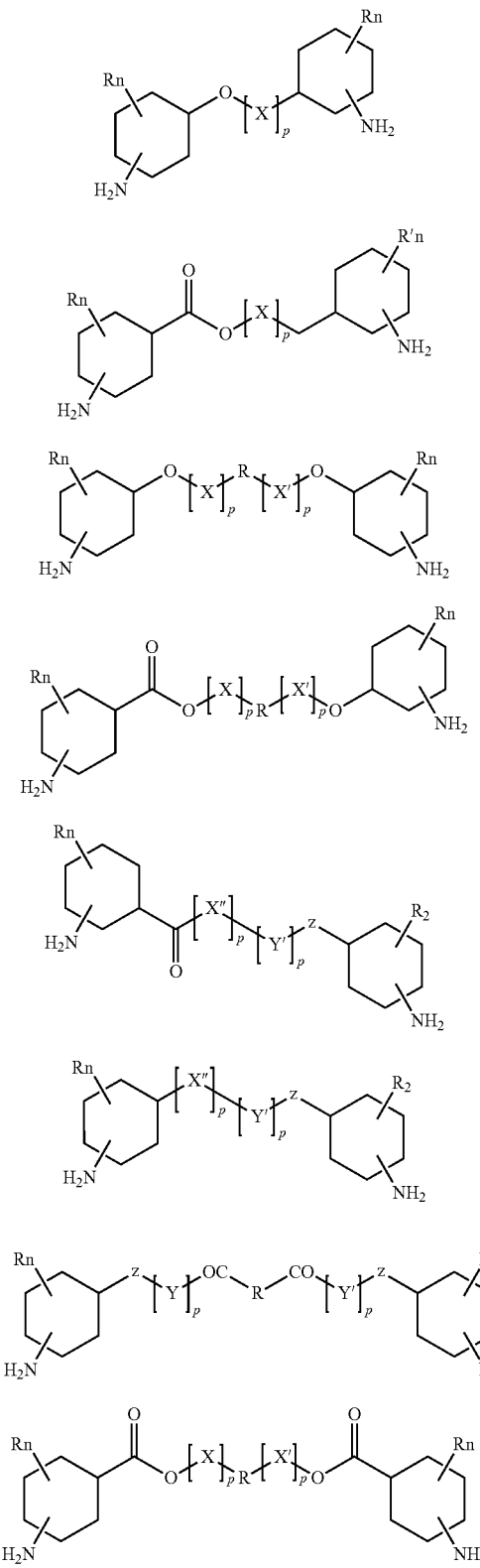

wherein each X, X', X", Y, Y', y, n, z', Rn and R are as defined above.

Preferred cyclic aliphatic diamine-based monomers are the cyclohexane-containing compounds (23)-(30), which are related to their aromatic counterparts (16)-(22) formally by reduction of the benzene rings to cyclohexane rings. As for the corresponding cycloaliphatic diisocyanate monomers, the polymers prepared from such saturated diamine monomers have beneficially reduced color, improved transparency and are non-yellowing.

Another aspect of the present invention is directed to methods of preparing diamines and diisocyanates containing only monomeric units containing (X)p, where p is 1, and which contain at least one compound having formula (16), (17), (1), or (2):

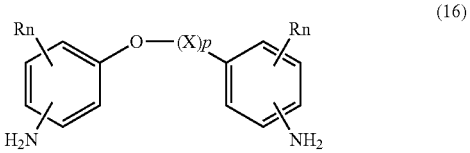

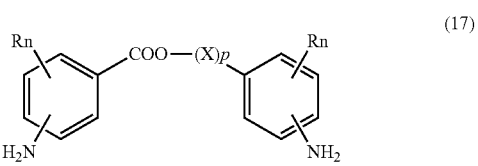

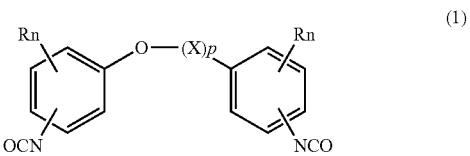

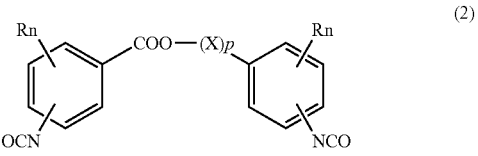

wherein each X, and Rn are as defined above.

Polymeric Moieties and Methods of Preparation Thereof

Processes for preparing polymers of the invention are provided as further embodiments of the invention and are illustrated by the following general methods:

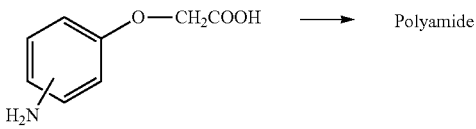

Polyamides can be prepared by self condensation or by reacting with another amino acid (HOOC—R—NH$_2$).

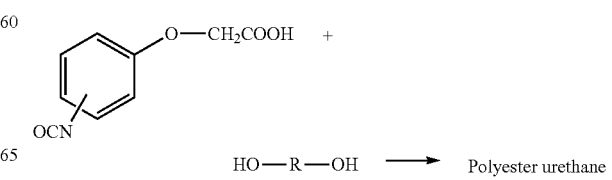

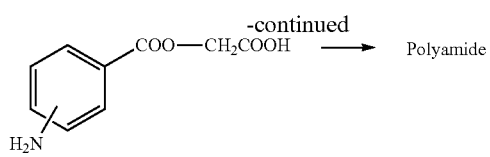

Again, polyamides can be prepared by self condensation or by reacting with a different amino acid (HOOC—R—NH$_2$).

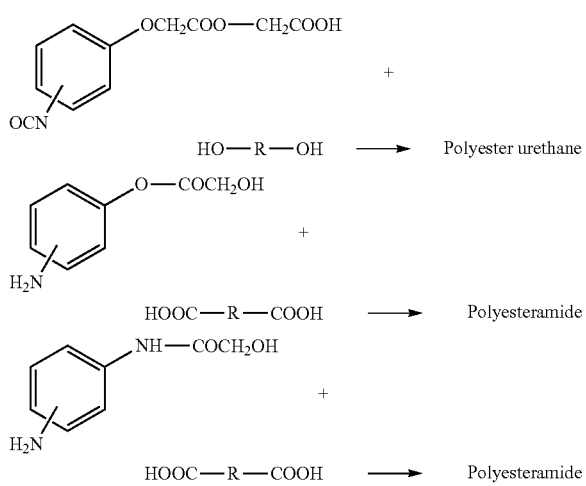

The monomer compounds of the invention can be used to polymerize biocompatible, biodegradable polyurethanes, polyester urethanes, and polyamides useful in a variety of applications where delivery of a biologically active compound is desired. Examples of such applications include, but are not limited to, medical, dental and cosmetic uses.

In another embodiment, copolymers of the absorbable polymers of this invention can be prepared by preparing a prepolymer under melt poly-condensation conditions, followed by adding at least one lactone monomer or lactone prepolymer. The mixture is then subjected to the desired conditions of temperature and time to copolymerize the prepolymer with the lactone monomers.

The polymers of the invention are prepared in accordance with methods commonly employed in the field of synthetic polymers to produce a variety of useful products with valuable physical and chemical properties. The polymers are readily processed into pastes or can be solvent cast to yield films, coatings, microspheres and fibers with different geometric shapes for the design of various medical implants, and may also be processed by compression molding and extrusion.

Polyurethanes, polyester urethanes, and polyamides prepared in accordance with the present invention have average molecular weights of about 1500 to about 100,000 calculated by Gel Permeation Chromatography (GPC) relative to narrow molecular weight polystyrene standards. Preferred polyurethanes, polyester urethanes, and polyamides have average molecular weights of about 1500 up to about 100,000 calculated by Gel Permeation Chromatography (GPC) relative to narrow molecular weight polystyrene standards. Preferred Polyurethanes, polyester urethanes, and polyamides have average molecular weights of about 1500 up to about 40,000.

Processes for preparing polyamides of the invention are provided as further embodiments of the invention and are illustrated by the following general method:

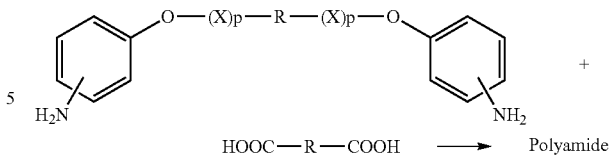

The diamines can also be reacted with diisocyanates (OCN—R—NCO) to prepare biodegradable polyureas.

Processes for preparing polyurethanes of the invention are provided as further embodiments of the invention and are illustrated by the following general procedure:

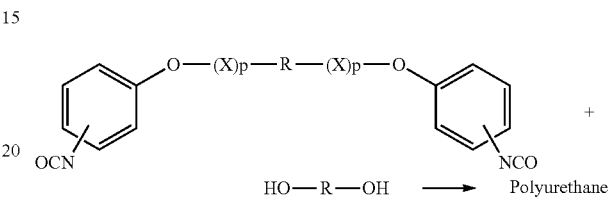

These isocyanates can also be reacted with diamines (H$_2$N—R—NH$_2$) to prepare biodegradable polyureas Chain Extenders: the nature of the chain extender group "R" in the polymers of the invention is not very critical provided that the polymer of the invention possesses acceptable mechanical properties and release kinetics for the selected therapeutic application. The chain extender group R is typically a divalent organic radical having a molecular weight of about 60 to about 5000. More preferably, R has a molecular weight of about 100 to about 1000, and may contain oxygen atoms, sulfur atoms and/or ester groups.

The chain extender group may be biologically inactive, or may itself possess biological activity. The chain extender group can also be a polyalkylene oxide, such as polyethylene oxide. The chain extender group can also be a polyester derived from at least one lactone monomer, such as glycolide, lactide, p-dioxanone, trimethylenecarbonate, or caprolactone. The chain extender group can also comprise other functional groups (including hydroxy groups, amine groups, carboxylic acids, and the like) that can be used to modify the properties of the polymer (e.g. for branching, for cross linking).

The mechanical properties, such as ultimate tensile strength, of the polyurethanes of the present invention can in some cases be influenced primarily by the polyol component as opposed to the hard segment as in typical segmented polyurethanes.

Suitable diols or polydiols for use in the present invention are diol or diol repeating units with up to 8 carbon atoms. Examples of suitable diols include diols selected from 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof. Examples of preferred polydiols include polydiols selected from polyethylene glycol and polypropylene glycol with molecular weights of 500-10000.

Preferably, the polyurethane is of the type known as a segmented polyurethane, which is characterized by a formation of repeating soft and hard blocks formed from a polyol component, a diisocyanate component and an optional chain extender, and can occur in a linear, branched or networked form. The term chain extender is intended to refer to a multi-functional molecule which may be reacted with the previously synthesized pre-polymer to generate a high molecular weight polymer, a polyurethane for example. However, the formation of polyurethanes may also be carried out using such processes as a single step process involving reaction of the chain extender together with the diisocyanate and the polyol, without the formation of a prepolymer.

Preferably, the polyol component is selected according to the component's toxicity, which is liberated when the polymer is broken down. Two examples of appropriate polyols are polyethylene oxide and polycaprolactone diol. Others may be suitable in some cases.

The constituents making up the polyurethane can be selected so as to be biodegradable to substantially nontoxic constituents. The term 'substantially non-toxic' is intended to refer to materials which when present in the body are physically tolerated and, more specifically, do not cause appreciable cell death (cytotoxicity) or detrimental alteration of normal cell function (such as a mutagenic response). This would of course depend on where and how the material is applied. Detailed in vivo tests may be appropriate to determine the effect of the material on the neighboring cells.

Depending on the synthesis route selected, these cleavable sites may be regularly spaced along the length of the chain extender, thereby giving the segmented polyurethane a biodegradability which is, by some measure, predictable. Biodegradability is influenced by a number of factors, including the number of susceptible sites, and crystallinity.

The hydrophilicity of the polymer, that is, the extent to which water is accessible to the polymer matrix and the susceptible sites, may also influence the degradability. In those cases where the chain extender has enzyme recognizable side groups, the access of water to the surface of the matrix should increase the rate at which the enzyme can catalyze the reaction between water and the hydrolyzable cleavage sites.

The number of cleavage sites also influences biodegradability. The higher the number of sites generally, the greater the rate of degradation. Preferably, the cleavable site is an ester site and, more preferably, the cleavable ester site is adjacent one or more amino acids. This provides segmented polyurethanes with cleavable sites in its chain extender that may be engineered to be recognizable by an enzyme.

In one embodiment, the diisocyanate is reacted with the polyol under suitable conditions to form a prepolymer; the prepolymer is then reacted with the chain extender, again under suitable conditions, to form the polyurethane.

Alternatively, multi-functional components can be employed to produce a cross-linked network, and hence non-linear, segmented polyurethane. This could be achieved by the use of a branched complex bearing more than two hydroxyl groups, such as for example a triol, for example. In another case, certain amino acids may also contribute to the formation of a networked polymer. Lysine for example, having an amine group on its side chain, may be reacted with such sites as a isocyanate group on the diisocyanate. Additionally, several lysines may be present in the amino acid segment thereby providing potential bonding sites between each corresponding amine and another site such as an isocyanate group. Thus, such multi-functional components readily allow for the formation of nonlinear segmented polyurethanes.

In one embodiment, substantially non-toxic degradable polyurethanes can be formed from amino acids and substantially non-toxic diols, in such a manner, to be useful as biomaterials for a variety of applications such as artificial skin, wound dressings, tissue engineering scaffolds and the like. The polyurethane materials may be formed by melt or solvent processing techniques such as dissolving the polymer into a solvent, pouring the mixture onto a flat sheet or into a mold and evaporating the solvent, with the polymer remaining therein. Other melt processing techniques may be available by melting a blank of polyurethane and manipulating it into a shape as desired, including tubes or fibers. A porous polyurethane may be formed in a number of ways, including the addition of a gas (typically carbon dioxide) into the polymerization reaction, and trapping the gas into the polymer structure. Alternatively, salt crystals can be added to the solvent polymer mixture during casting wherein the salt is not dissolved. The mixture may be deposited into a dish causing the solvent to evaporate, with the salt material being removed by subsequent washing with water.

One embodiment of the invention is directed to a polymer containing at least one repeating unit of at least one of the compounds (1)-(30), above, wherein each X is independently selected from the group consisting of:

—$CH_2COO$— (glycolic acid moiety),

—$CH(CH_3)COO$— (lactic acid moiety),

—$CH_2CH_2OCH_2COO$— (dioxanone moiety), and

—$CH_2CH_2CH_2CH_2CH_2COO$— (caprolactone moiety);

each X' represents a member independently selected from the group consisting of:

—$OOCCH_2$— (glycolic acid moiety);

—$OOCCH(CH_3)$— (lactic acid moiety);

—$OOCCH_2OCH_2CH_2$— (dioxanone moiety);

—$OOCCH_2CH_2CH_2CH_2$— (caprolactone moiety);

each X" represents a member independently selected from the group consisting of:

—$OCH_2CO$— (glycolic acid moiety);

—$OCH(CH_3)CO$— (lactic acid moiety);

—$OCH_2CH_2OCH_2CO$— (dioxanone moiety);

—$OCH_2CH_2CH_2CH_2CH_2CO$— (caprolactone moiety);

each Y is independently selected from the group consisting of:

—$COCH_2O$— (glycolic ester moiety);

—$COCH(CH_3)O$— (lactic ester moiety);

—$COCH_2OCH_2CH_2O$— (dioxanone ester moiety); and

—$COCH_2CH_2CH_2CH_2CH_2O$— (caprolactone ester moiety); and each Y' represents a member independently selected from the group consisting of:

—$OCH_2CO$— (glycolic ester moiety);

—$OCH(CH_3)CO$— (lactic ester moiety);

—$OCH_2CH_2OCH_2CO$— (dioxanone ester moiety);

—$OCH_2CH_2CH_2CH_2CH_2CO$— (caprolactone ester moiety).

Further aspects of the invention comprise compositions and articles comprising the above polymers.

In another embodiment, the present invention is directed to absorbable polyurethanes comprising at least one cyclohexane-based compound selected from structural formulas (8)-(15).

Accordingly, another aspect of the present invention is directed to an absorbable polymer comprising at least one compound selected from cyclohexane-based diamines (23)-(30).

Accordingly, yet another aspect of the present invention is directed to the preparation of an absorbable polymer derived from at least one compound selected from:

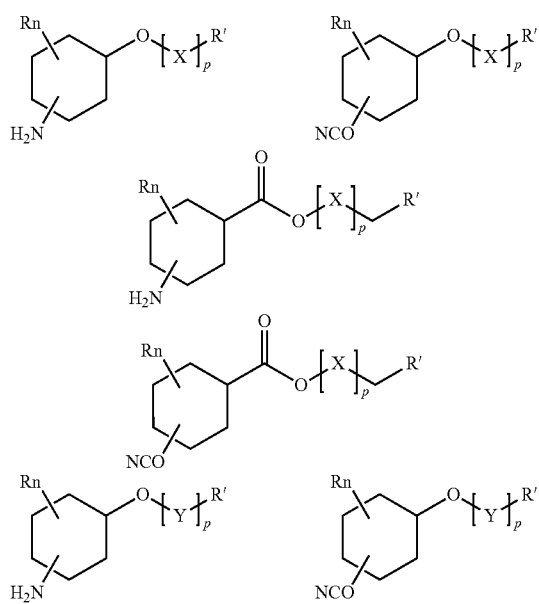

wherein each X represents a member independently selected from
—CH$_2$COO— (glycolic acid moiety);
—CH(CH$_3$)COO— (lactic acid moiety);
—CH$_2$CH$_2$OCH$_2$COO— (dioxanone moiety);
—CH$_2$CH$_2$CH$_2$CH$_2$CH$_2$COO— (caprolactone moiety);
—(CH$_2$)$_y$COO— where y is one of the numbers 2, 3, 4 or 6-24 inclusive, and
—(CH$_2$CH$_2$)$_{z'}$CH$_2$COO— where z' is an integer between 2 and 24 inclusive;
each Y represents a member independently selected from:
—COCH$_2$O— (glycolic ester moiety);
—COCH(CH$_3$)O— (lactic ester moiety);
—COCH$_2$OCH$_2$CH$_2$O— (dioxanone ester moiety);
—COCH$_2$CH$_2$CH$_2$CH$_2$CH$_2$O— (caprolactone ester moiety);
—CO(CH$_2$)$_m$O— where m is an integer between 2-4 and 6-24 inclusive, and
—COCH$_2$—O—(CH$_2$CH$_2$O)$_n$— where n is an integer between 2 and 24, inclusive;
each R' is hydrogen, benzyl or an alkyl group, the alkyl group being either straight-chained or branched; and p is an integer between 1 and 4, inclusive.

The polymers prepared by reacting the above amines or isocyanates with diols, such as HO—R—OH, or with diacids, such as HOOC—R—COOH, can include, without limitation, polyurethanes, polyamides, polyesterurethanes and polyesteramides. The R group can be biologically inactive, or can itself possess biological activity. The R group can also be a polyethylene oxide, a polyester derived from at least one lactone monomer, such as glycolide, lactide, p-dioxanone, trimethylenecarbonate, or caprolactone; other functional groups (including hydroxy groups, amine groups, carboxylic acids, etc), or diols or polyols having up to 8 carbon atoms, such as 1,2-ethanediol (ethylene glycol), 1,2-propanediol (propylene glycol), 1,3-propanediol, 1,4-butanediol, 1,5-pentanediol, 1,3-cyclopentanediol, 1,6-hexanediol, 1,4-cyclohexanediol, 1,8-octanediol and combinations thereof. Examples of preferred polydiols include polydiols selected from polyethylene glycol and polypropylene glycol with molecular weights of 500-10000, all of which can modify the properties of the polymer (e.g. for branching or for cross linking). Preferably, the Rn and R groups are selected independently to minimize the risk of toxicity when broken down or otherwise liberated.

A more preferred embodiment of the present invention comprises absorbable polymers containing at least one repeating unit having the structure of any of formulas (I)-(IV). Another more preferred embodiment comprises methods of preparing such units:

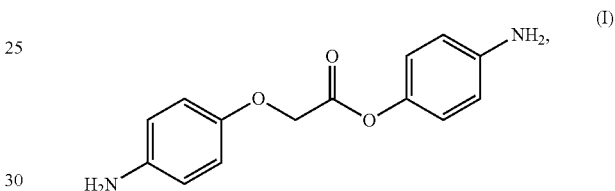

(I)

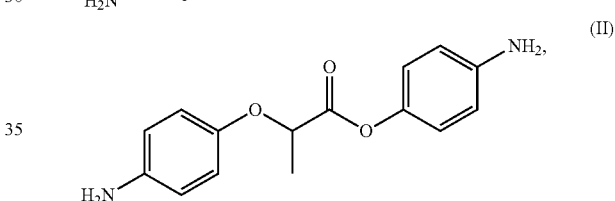

(II)

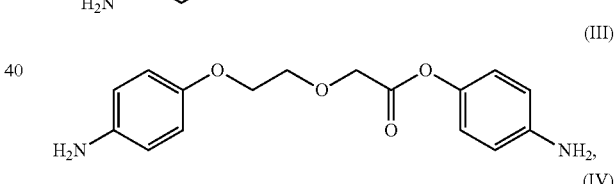

(III)

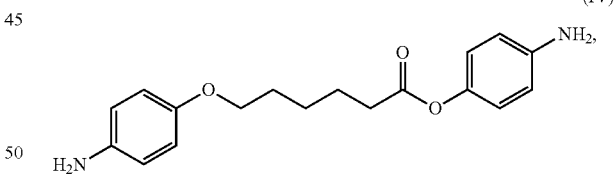

(IV)

In another preferred embodiment, absorbable polymers are disclosed containing at least one repeating unit having the structure of any of formulas (V)-(VIII):

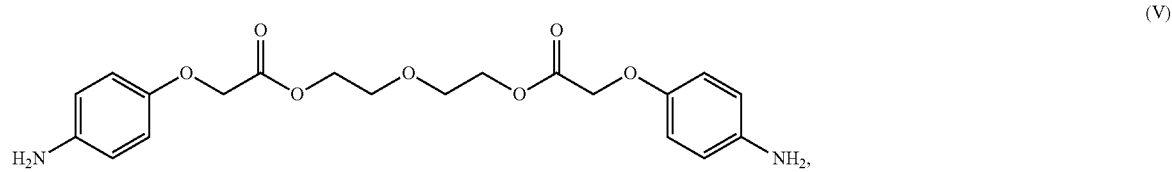

(V)

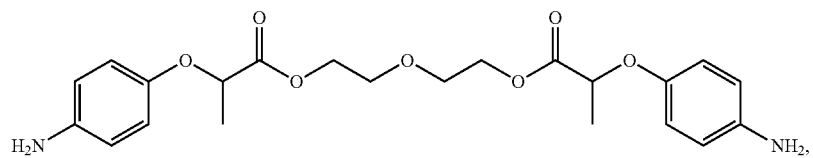
(VI)

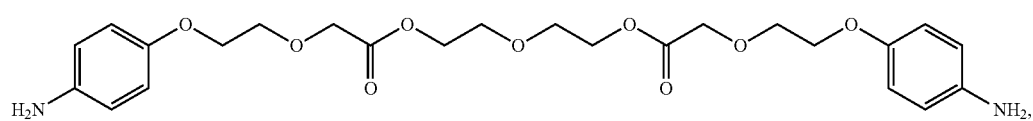
(VII)

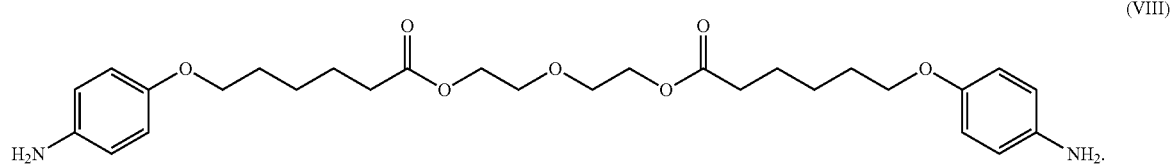
(VIII)

Still another aspect of the present invention comprises the preparation of absorbable polymers containing at least one repeating unit having the structure of any of formulas (IX)-(XII):

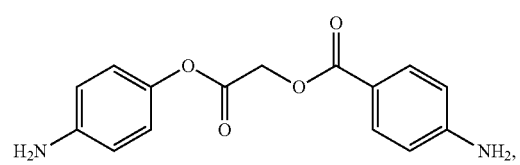
(IX)

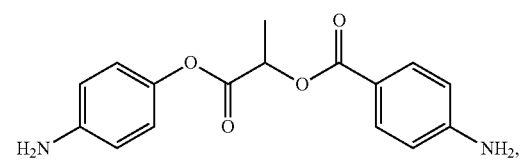
(X)

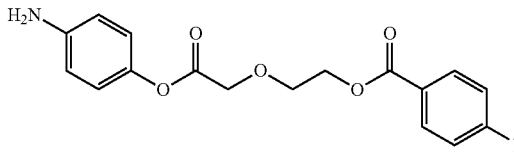
(XI)

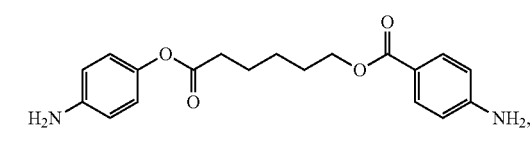
(XII)

Yet another aspect of the present invention comprises the preparation of absorbable polymers containing at least one repeating unit having the structure of any of formulas (XIII)-(XVI):

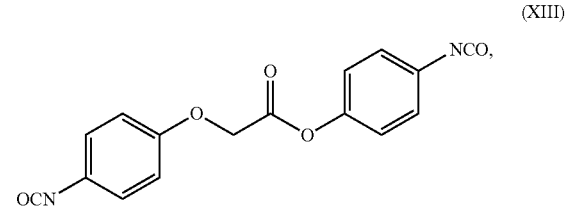
(XIII)

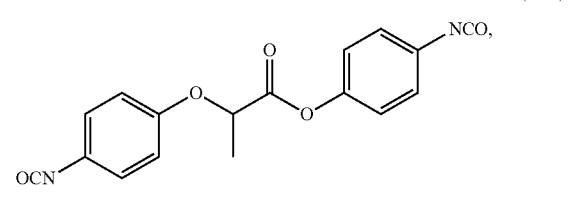
(XIV)

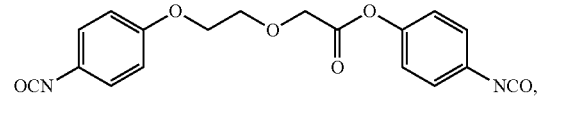
(XV)

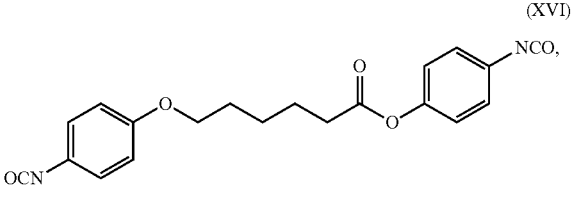
(XVI)

Another aspect of the present invention comprises the preparation of absorbable polymers containing at least one repeating unit having the structure of any of formulas (XVII)-(XX):

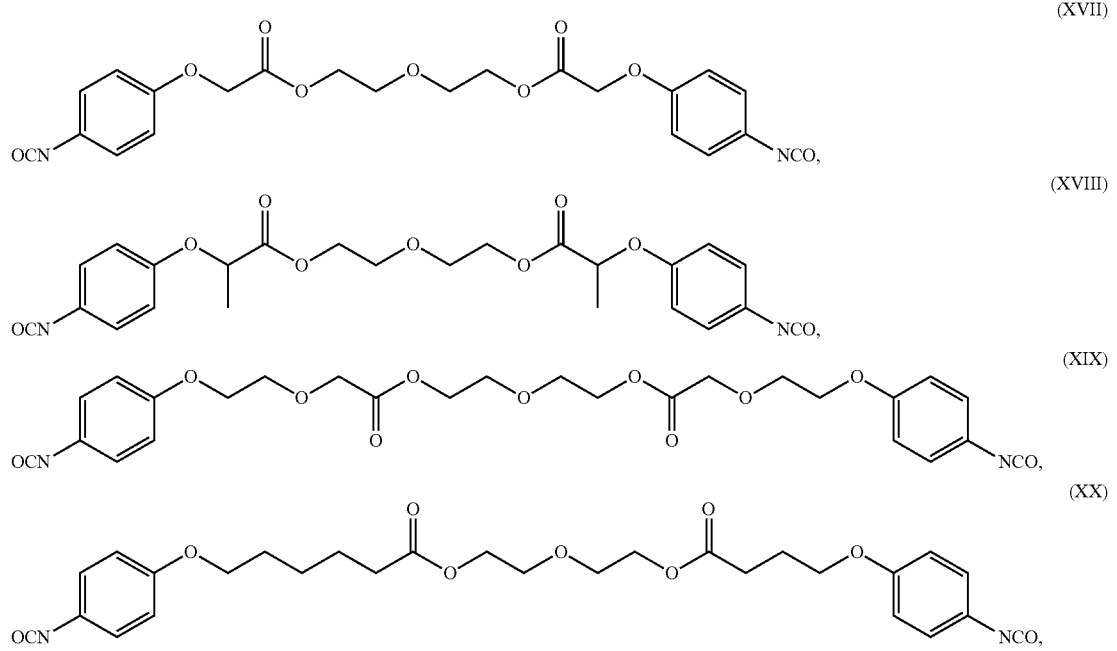
Still another aspect of the present invention comprises the preparation of absorbable polymers containing at least one repeating unit having the structure of any of formulas (XXI)-(XXIV):
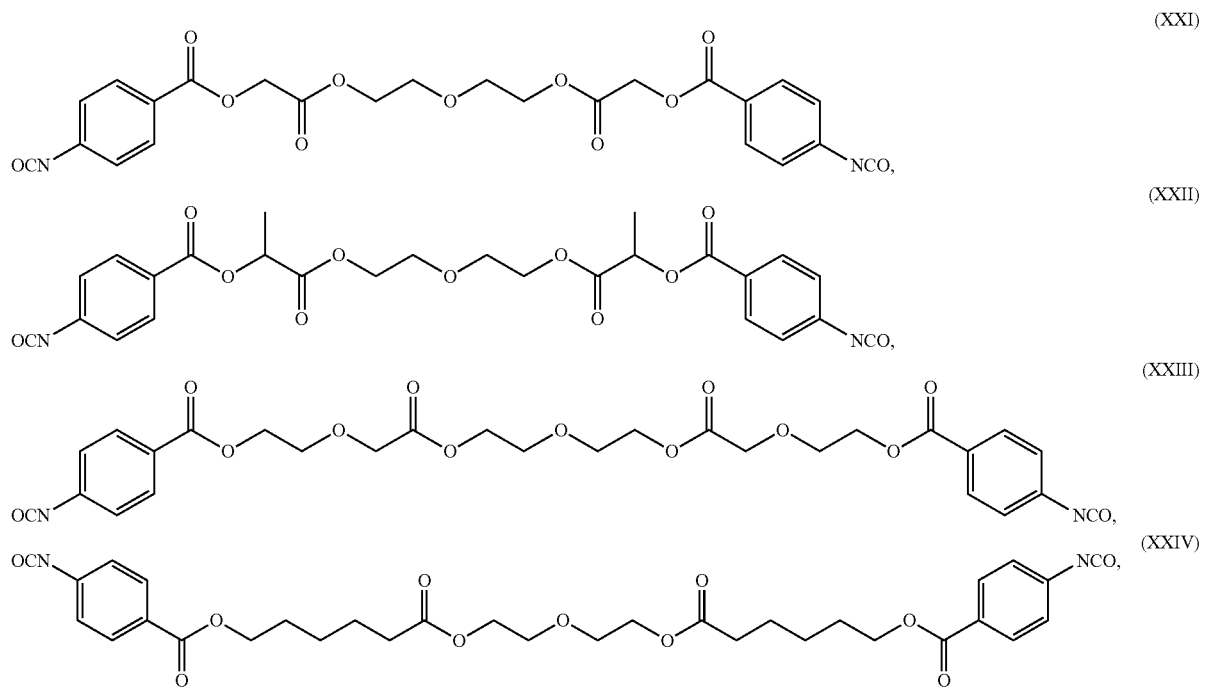
In yet another aspect of the present invention absorbable polymers are described containing at least one repeating unit having the structure of any of formulas (XXV)-(XXVIII):

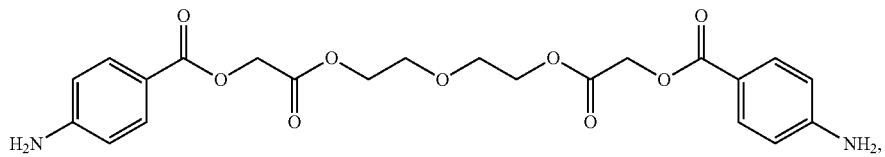
(XXV)

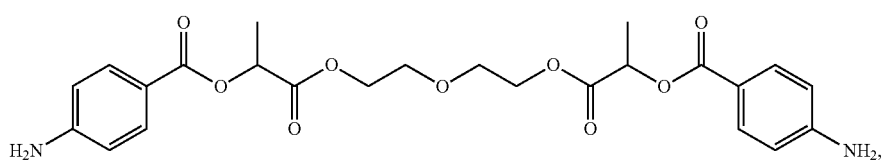
(XXVI)

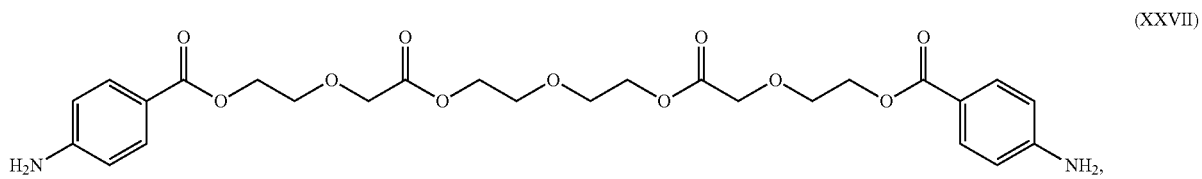
(XXVII)

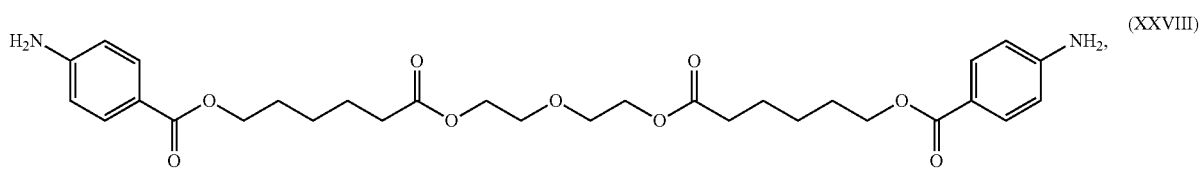
(XXVIII)

Another aspect of the present invention comprises the preparation of absorbable polymers containing at least one repeating unit having the structure of any of formulas (XXIX)-(XXXII):

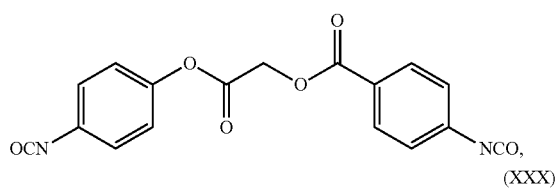
(XXX)

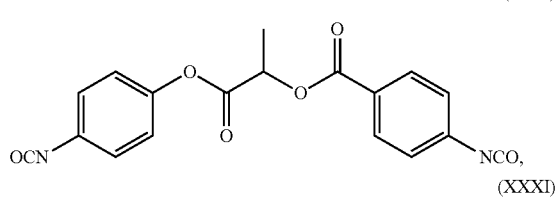
(XXXI)

-continued

(XXXII)

Another aspect of the present invention is directed to a polymer comprising at least one repeating unit of at least one compound (I)-(XXXII). Further aspects of the invention comprise compositions and articles comprising the above polymers.

Yet another aspect of the present invention is directed to methods and processes for preparing the biodegradable and bioabsorbable polymers of the invention from the monomers disclosed, vide supra, with or without the inclusion of other monomers. The polymerization processes typically used for the formation of polyurethanes, polyamides, etc., are well-known to those skilled in the art. Representative processes are provided in U.S. Pat. No. 7,773,352, which is incorporated herein by reference in its entirety.

Monocaprolactone diisocyanate can be prepared according to Scheme 1.

Scheme 1
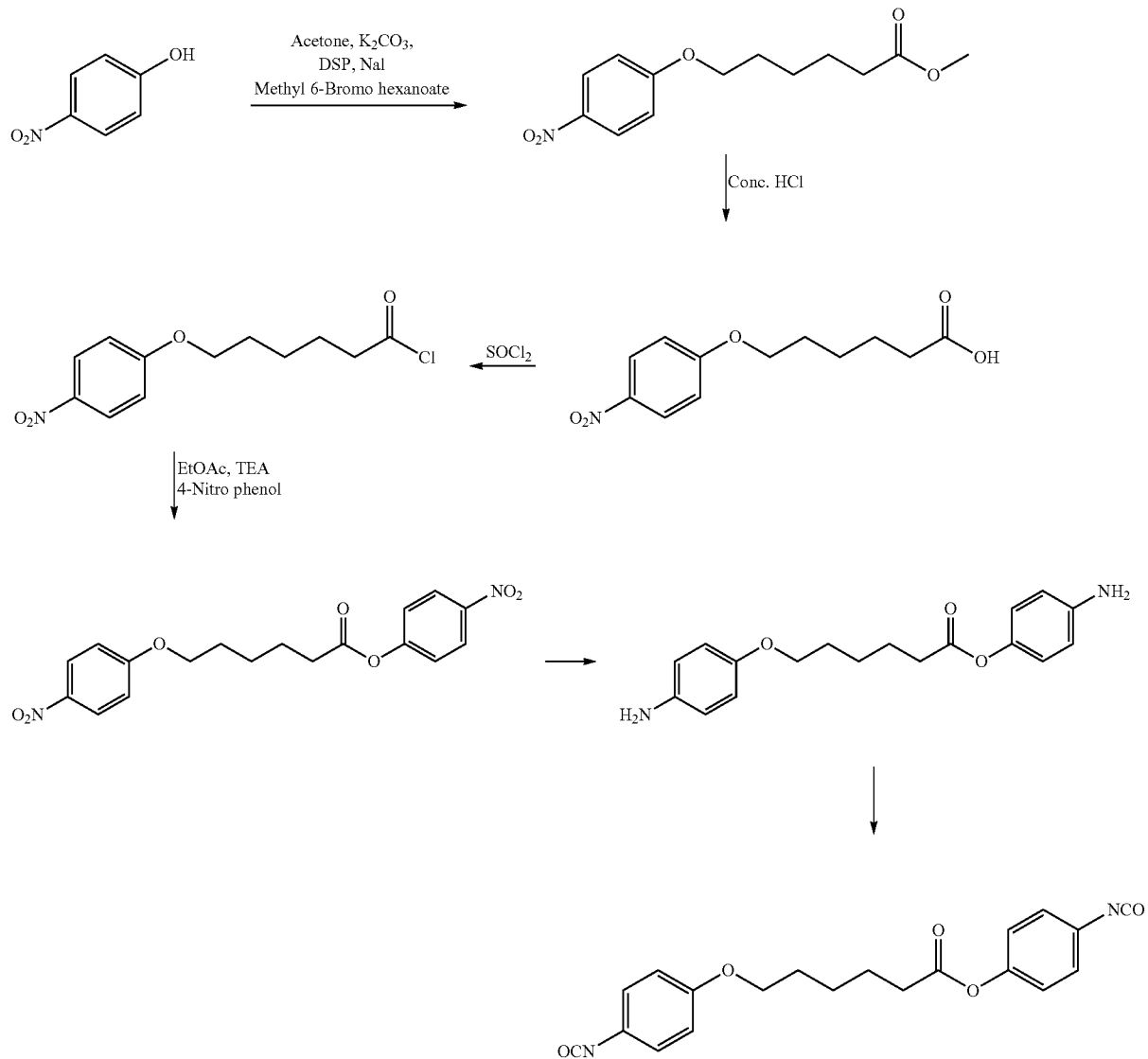
where DSP is disodium phosphate, and TEA is triethylamine.
In yet another embodiment of the present invention, processes for preparing polylactide diisocyanates are described following the procedures depicted in Scheme 2.
Scheme 2
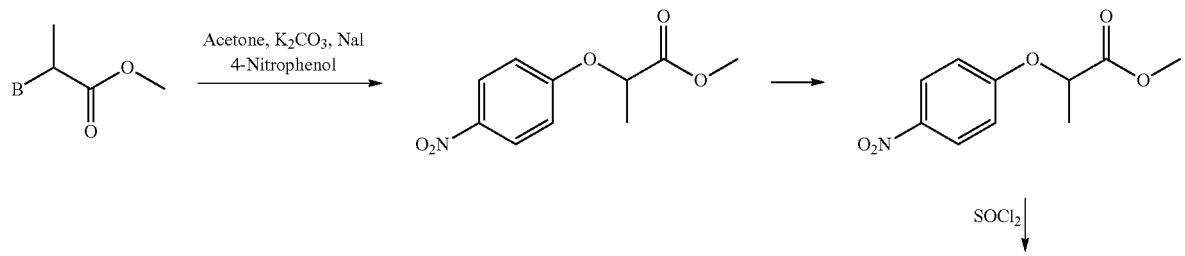

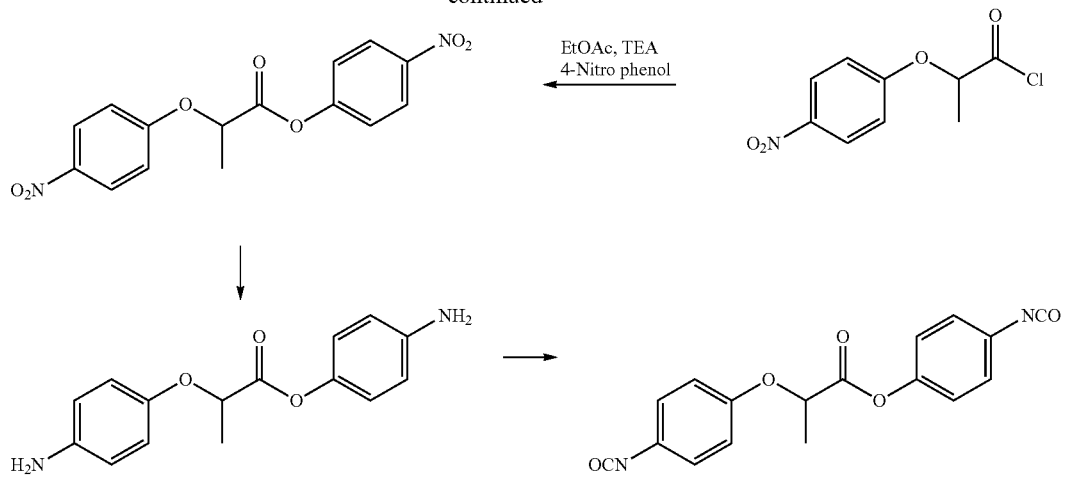
In another embodiment of the present invention, processes for preparing diethylene glycol diglycolate diisocyanate phenols are described according to the procedures depicted in Scheme 3.
Scheme 3
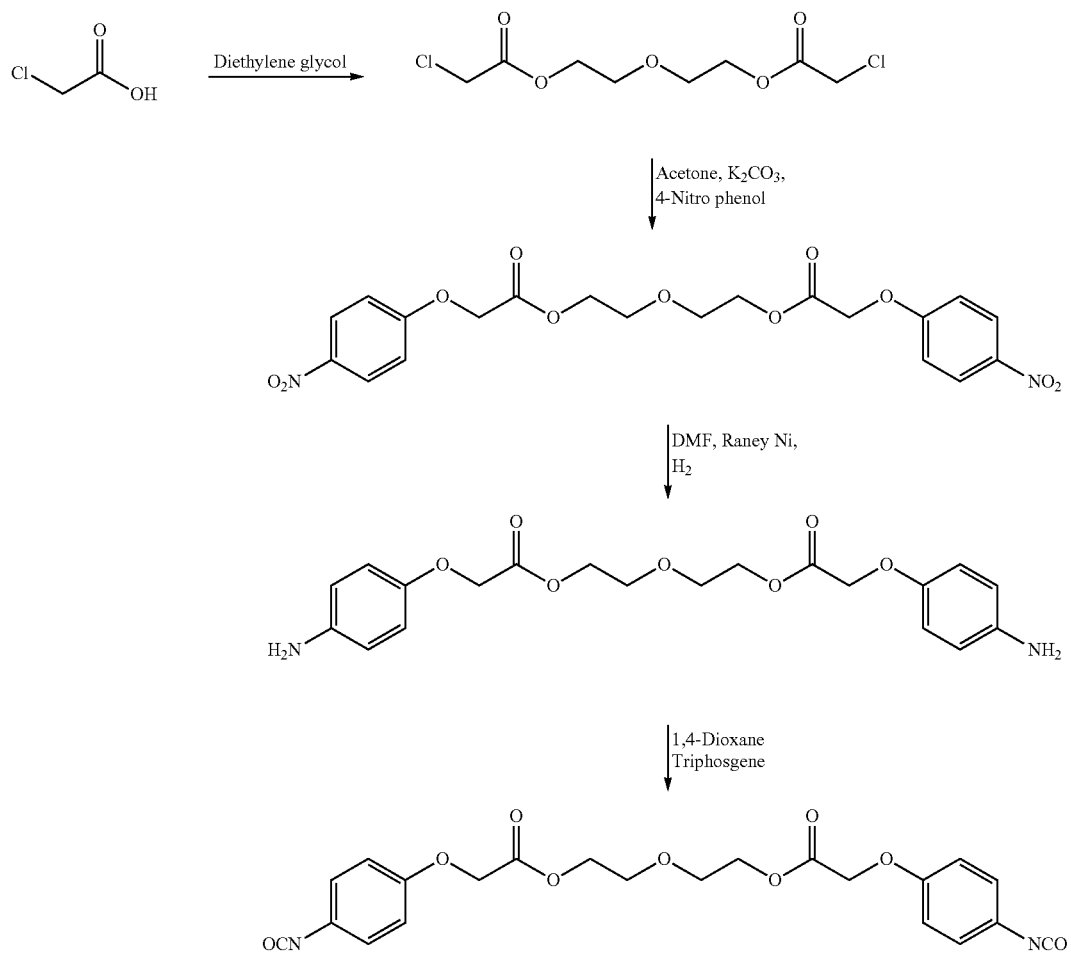

In another embodiment of the present invention, processes for preparing diethylene glycol dilactate diisocyanate phenols; (4-isocyanato-phenoxy)-propionic acid 2-{2-[2-(4-isocyanato-phenoxy)-propionyloxy]-ethoxy}-ethyl ester; are described according to the procedure depicted in Scheme 4.

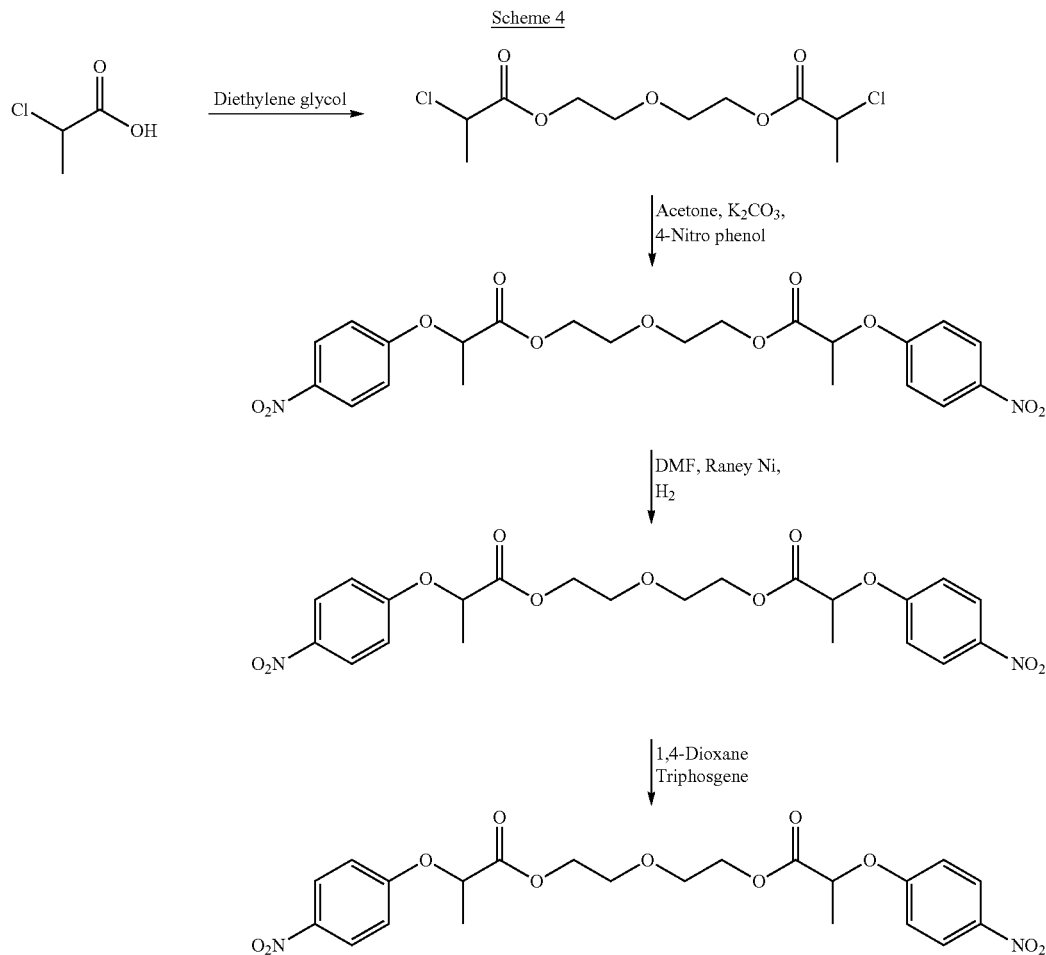

In another embodiment of the present invention, a process for preparing diethylene glycol caprolactone diisocyanate phenols is described according to the procedures depicted in Scheme 5.

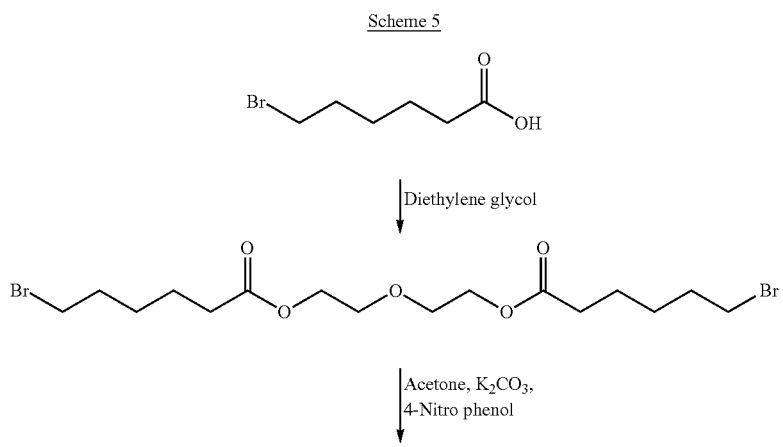

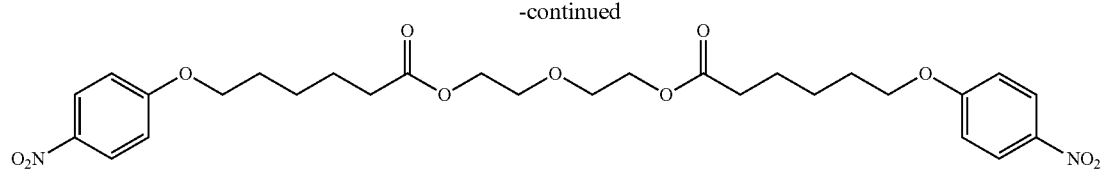
↓ Reduction
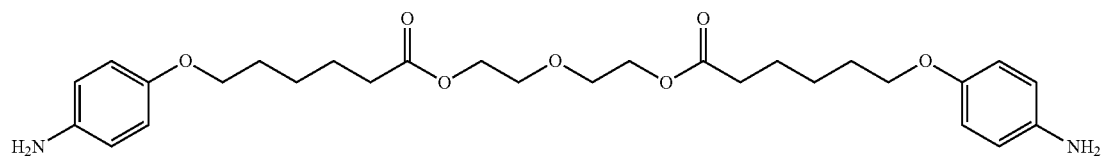
↓ 1,4-Dioxane
Triphosgene
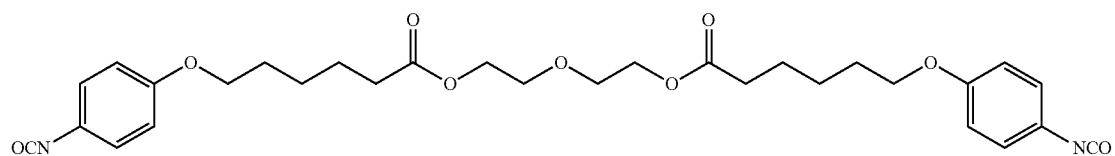
In another embodiment of the present invention, processes for preparing diethylene glycol caprolactone diisocyanate benzoic acid are described according to the procedures depicted in Scheme 6.
Scheme 6
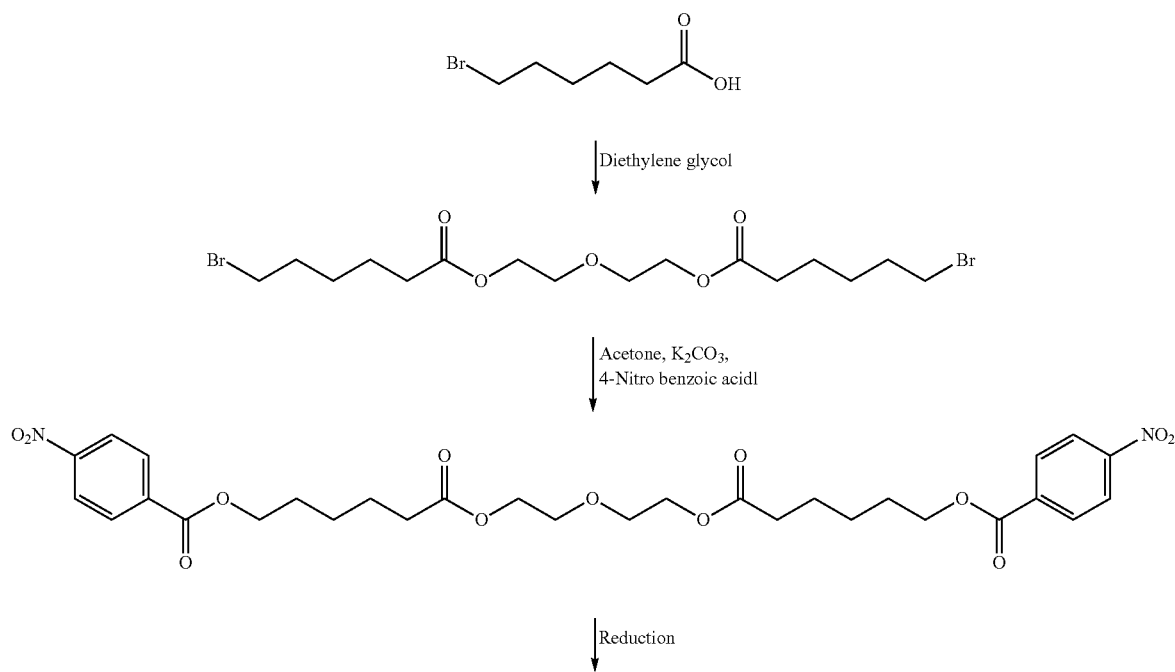
↓ Reduction

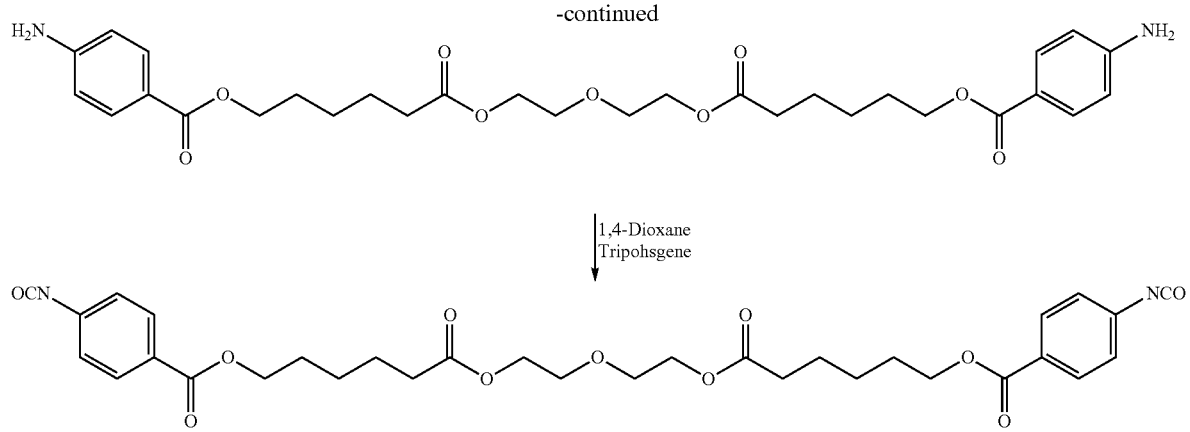

Another aspect of the present invention focuses on the hydrophilicity of the polymer which may also influence the degradability, that is, the extent to which water is accessible to the polymer matrix. In those cases where the chain extender has enzyme recognizable side groups, the access of the water to the surface of the matrix should increase the rate at which an enzyme can catalyze the reaction between water and the hydrolyzable cleavage sites.

The number of cleavage sites also influences biodegradability. The higher the number of sites generally, the greater the rate of degradation. Preferably, the cleavable site is an ester site and, more preferably, the cleavable ester site is adjacent to one or more amino acids. This provides segmented polyurethanes with cleavable sites in its chain extender that may be arranged to be recognizable by enzymes. In this aspect of the invention, the rate of degradation is controlled to achieve the preferred therapeutic indication.

In one embodiment, the diisocyanate is reacted with a polyol, under suitable conditions to form a prepolymer; and the prepolymer is then reacted with the R group, again under suitable conditions, to form the polyurethane.

In one embodiment, substantially non-toxic biodegradable polyurethanes can be formed from amino acids and substantially non-toxic diols, in such a manner so as to be useful as biomaterials for a variety of applications such as artificial skin, wound dressings, tissue engineering scaffolds and the like. The polyurethane materials may be formed by solvent processing techniques such as dissolving the polymer into a solvent, pouring the mixture onto a flat sheet or into a mold and evaporating the solvent, with the polymer remaining therein. Melt processing techniques can include, for example, melting a blank of polyurethane and manipulating it into shapes, such as tubes and fibers, as desired. A porous polyurethane is formed in a number of ways, including the addition of a gas (typically carbon dioxide) into the polymerization reaction, and trapping the gas into the polymer structure. Alternatively, salt crystals can be added to the solvent polymer mixture during casting wherein the salt is not dissolved. The mixture is deposited into a dish causing the solvent to evaporate, with the salt material being removed by washing with water.

The polyurethane materials disclosed herein may be used in a number of different forms and in a range of applications, both in the biomedical field and others. The material can be fabricated by casting or other molding techniques to form a substrate, which can be used alone or combined with other substrates to form homogenous multi-layered materials. Such multilayered homogeneous polyurethane materials may be formed with layers having different degrees of degradability. Such substrates may range in thickness from about 1 micron to about 5 millimeters for applications suitable for skin repair and the like, and more particularly from about 10 microns to about 3.5 millimeters, and still more particularly from about 50 microns to about 2 millimeters. The thinner the substrate, the more care is needed in handling it.

For bone regeneration and the like, the polyurethane material may range in thickness from about 1 cm to about 5 cm or more, depending on the specific application, including the dimensions of the bone being regenerated. Preferably, the thickness is about 1 cm to about 5 cm.

In another aspect of the present invention the polyurethanes are of the segmented variety which are bioabsorbable. In this aspect of the invention the mechanical properties, such as ultimate tensile strength, of the polyurethanes can, in some cases, be influenced primarily by the polyol as opposed to the hard segment, as for typical segmented polyurethanes. Preferably, such polyurethanes are of the type which is characterized by the formation of repeating soft and hard blocks formed from such intermediates as a polyol, a diisocyanate and a chain extender, R, and can occur in a linear, branched or networked form. Chain extenders may include multi-functional molecules which may be reacted with the previously synthesized pre-polymer to generate a high molecular weight polyurethane for example. However, the formation of polyurethanes may also be carried out using such processes as a single step process involving reaction of the chain extender with the diisocyanate and the polyol, which process does not require the formation of a prepolymer.

In another aspect of the present invention, the polymers of the present invention may contain a cleavable site which is preferably an ester site and, more preferably, the cleavable ester site is adjacent one or more amino acids. This provides segmented polyurethanes with cleavable sites in its chain extender, which sites may be arranged to be recognizable by enzymes.

In another embodiment of the present invention, the inventive polymers can be used as a pharmaceutical carrier in a drug delivery matrix. The matrix is formed by mixing the polymer with a therapeutic agent. A vast variety of different therapeutic agents can be used in conjunction with the polymers of the invention. In general, therapeutic agents administered via the pharmaceutical compositions of the invention include, without limitation antiinfectives such as antibiotics and antiviral agents; analgesics and analgesic combinations; anorexics; antihelmintics; antiarthritics; anti-asthmatic agents; anticonvulsants; antidepressants; antidiuretic agents; antidiarrheals; antihist-amines; antiinflammatory agents; antimigraine preparations; antinauseants; antineo-plastics; antiparkinsonism drugs; antipruritics; antipsychotics; antipyretics, antispas-modics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; para-sympatholytics; psychostimulants; sedatives; tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention is formulated by mixing one or more therapeutic agents with the polymer. The therapeutic agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is entirely optional. Other suitable additives may be formulated with the polymers of this invention and pharmaceutically active agents or compounds, however, if water is to be used it should be added immediately before administration.

The amount of therapeutic agent will be dependent upon the particular drug employed and medical condition being treated. Typically, the amount of drug represents about 0.001% to about 70%, more typically about 0.01% to about 50%, and most typically about 0.1% to about 20% by weight of the matrix.

The quantity and type of polymer incorporated into a parenteral dosage form will vary depending on the release profile desired and the amount of drug employed. The product may contain blends of polymers of this invention to provide the desired release profile or consistency to a given formulation.

The polymers of this invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (over one to 2,000 hours, preferably two to 800 hours) of effective amounts (0.0001 mg/kg/hour to 10 mg/kg/hour) of the drug. This dosage form can be administered as necessary depending on the subject being treated, the severity of the affliction, the judgment of the prescribing physician, and the like.

Individual formulations of drugs and polymers of this invention may be tested in appropriate in vitro and/or in vivo models to achieve the desired drug release profiles. For example, a drug could be formulated with a polymer of this invention and orally administered to an animal. The drug release profile is monitored by appropriate means, such as by taking blood samples at specific times and assaying the samples for drug concentration. Following this or similar procedures, those skilled in the art are able to formulate a variety of formulations having the desired release profile.

The polyurethanes, polyureas, polyamideurethanes, and/or polyureaurethanes of the invention may be formed into various articles for surgical and medical uses including, without limitation:

a. burn dressings,
b. hernia patches,
c. medicated dressings,
d. fascial substitutes,
e. gauze, fabric, sheet, felt or sponge for liver hemostasis,
f. gauze bandages,
g. arterial graft or substitutes,
h. bandages for skin surfaces,
i. suture knot clip,
j. orthopedic pins, clamps, screws, and plates,
k. clips (e.g., for vena cava),
l. staples,
m. hooks, buttons, and snaps,
n. bone substitutes (e.g., mandible prosthesis),
o. intrauterine devices (e.g., spermicidal devices),
p. draining or testing tubes or capillaries,
q. surgical instruments,
r. vascular implants or supports,
s. vertebral discs,
t. extracorporeal tubing for kidney and heart-lung machines,
u. artificial skin, and the like.

The polyurethanes, polyureas, polyamideurethanes, and/or polyureaurethanes of the invention may be formed into surgical articles using any known technique, such as, for example, extrusion, molding and/or solvent casting. The polyurethanes, polyureas, polyamideurethanes, and/or polyureaurethanes may be used alone, blended with other bioabsorbable compositions, or in combination with non-bioabsorbable components. A wide variety of surgical articles may be manufactured from the polyurethanes, polyureas, polyamideurethanes, and/or polyureaurethanes described herein. These include but are not limited to clips and other fasteners, staples, sutures, pins, screws, prosthetic devices, wound dressings or coverings, burn dressings or coverings, drug delivery devices, anastomosis rings, stents, stent coatings, films, scaffolds, polyurethane foams, reticulated foams and other implantable medical devices. Examples of medical implantable devices include prosthetic devices, stents, sutures, staples, clips and other fasteners, screws, pins, films, meshes, drug delivery devices or systems, anastomosis rings, surgical dressings and the like. In some preferred embodiments, the surgical articles or components thereof include stents, stent coatings, wound coverings, burn coverings, foams, tissue engineering scaffolds, films, implantable medical devices, and/or controlled drug delivery systems, more preferably stents, stent coatings, wound and/or burn coverings, and/or controlled delivery systems. In certain other preferred embodiments, the surgical articles or components thereof include sutures, ligatures, needle and suture combinations, surgical clips, surgical staples, surgical prosthetic devices, textile structures, couplings, tubes, supports, screws, or pins. In certain preferred drug delivery systems, the systems comprise a polyurethane, polyurea, polyamideurethane, and/or polyureaurethane in admixture with a biologically or pharmaceutically active agent. Non-limiting examples of polymeric carriers in such drug delivery systems and/or pharmaceutical compositions include self-supporting films, hollow tubes, beads, and/or gels. Other preferred uses of the surgical articles include their use as scaffolds for tissue engineering comprising a porous structure for the attachment and proliferation of cells.

Preferably, the surgical and medical uses of the filaments, films, and molded articles of the present invention include, but are not necessarily limited to knitted products, woven or non-woven, and molded products including, burn dressings, hernia patches, medicated dressings, facial substitutes, gauze, fabric, sheet, felt or sponge for liver homeostasis, gauze bandages, arterial graft or substitutes, bandages for skin surfaces, suture knot clip, orthopedic pins, clamps, screws, and plates, clips (e.g., for vena cava), staples, hooks, buttons, and snaps, bone substitutes (e.g., mandible prosthesis), bone void fillers, bone cements, intrauterine devices (e.g., spermicidal devices), draining or testing tubes or capillaries, surgical instruments, vascular implants or supports, vertebral discs, extracorporeal tubing for kidney and heart-lung machines, artificial skin and others.

The polyurethanes, polyureas, polyamideurethanes, and/or polyureaurethanes disclosed herein may also be used to fabricate degradable containers and packaging materials which can degrade in landfills in contrast to existing non-degradable materials which present environmental concerns.

The polyurethane material is believed to be especially useful for use as a tissue engineering scaffold, i.e., as a structure for the growth or regeneration of tissue. Polyurethanes may lend themselves to such uses since enzyme-catalyzed degradation may in some cases occur concurrently with the migration or growth of cells into the material, while desirably degrading in the process into its substantially non-toxic constituents. It is also possible, in some cases, that cells migrating into or located adjacent the matrix may themselves exude proteolytic enzymes that will mediate hydrolytic cleavage.

Such tissue engineering scaffolds may have applications in the regeneration of skin and other organs, bone, cartilage, ligaments, tendons, bladder and other tissues. The polyurethane material may also be useful in the production of sutures, which require good mechanical strength, as well as in the production of drug release matrices, in view of their need for degradation to non-toxic materials. The polyurethane material may also be useful for non-biomedical applications, where degradability into substantially non-toxic constituents is an asset. The polyurethane material lends itself to sterilization by such techniques as gamma radiation and ethylene oxide treatments.

Fibers made from the present polyurethanes, polyureas, polyamideurethanes, and/or polyureaurethanes can be knitted or woven with other fibers, either bioabsorbable or non-bioabsorbable, to form meshes or fabrics. Compositions including these polyurethanes, polyureas, polyamideurethanes, and/or polyureaurethanes may also be used as bioabsorbable coatings for surgical devices.

Another aspect of the invention is directed to compositions containing the polyurethanes, polyureas, polyamideurethanes, and/or polyureaurethanes described herein which may be used to make reinforced composites. Thus, for example, the polyurethane, polyurea, polyamideurethane, and/or polyureaurethane composition may form the matrix of the composite and may be reinforced with bioabsorbable or non-bioabsorbable fibers or particles. Alternatively, a matrix of any bioabsorbable or non-bioabsorbable polymer composition may be reinforced with fibers or particulate material made from compositions containing the polyurethanes, polyureas, polyamideurethanes, and/or polyureaurethanes described herein.

In a further embodiment, the polyurethanes, polyureas, polyamideurethanes, and/or polyureaurethanes described herein may be admixed with a filler. The filler may be in any particulate form, including granulate or staple fibers. While any known filler may be used, hydroxyapatite, tricalcium phosphate, bioglass or other bioceramics are the preferred fillers. Normally, from about 10 grams to about 400 grams of filler are mixed with about 100 grams of polymer. The filled, cross-linked polymers are useful, for example, as molding compositions.

It is further contemplated that one or more medico-surgically useful substances may be incorporated into compositions containing the polyurethanes, polyureas, polyamideurethanes, and/or polyureaurethanes described herein. Examples of such medico-surgically useful substances include, for example and without limitation, those which accelerate or beneficially modify the healing process when particles are applied to a surgical repair site. For example, articles made from compositions containing the presently disclosed polyurethanes, polyureas, polyamideurethanes, and/or polyureaurethanes may carry a therapeutic agent which will be deposited at the repair site. The therapeutic agent may be chosen for its antimicrobial properties, capability for promoting repair or reconstruction and/or new tissue growth. Antimicrobial agents such as broad spectrum antibiotics, for example and without limitation, gentamycin sulfate, erythromycin, or derivatized glycopeptides which are slowly released into the tissue, may be applied in this manner to aid in combating clinical and sub-clinical infections in a tissue repair site. To promote repair and/or tissue growth, one or several growth promoting factors may be introduced into the articles, e.g., fibroblast growth factor, bone growth factor, epidermal growth factor, platelet-derived growth factor, macrophage-derived growth factor, alveolar-derived growth factor, monocyte-derived growth factor, magainin, and the like. Examples of therapeutic indications include, without limitation, glycerol with tissue or kidney plasminogen activator to cause thrombosis, superoxide dismutase to scavenge tissue-damaging free radicals, tumor necrosis factor for cancer therapy or colony stimulating factor and interferon, interleukin-2 or other lymphokine to enhance the immune system.

Embodiments of the present invention are described with reference to the following Examples, which are presented for illustrative purposes only, and are not intended to limit the scope of the invention in any way.

EXAMPLES

In a preferred embodiment, monocaprolactone diisocyanate compounds are prepared according to Scheme 1 described above, according to the steps described in examples 1-6.

Example 1

Synthesis of 6-(4-nitrophenoxy)-hexanoic acid methyl ester

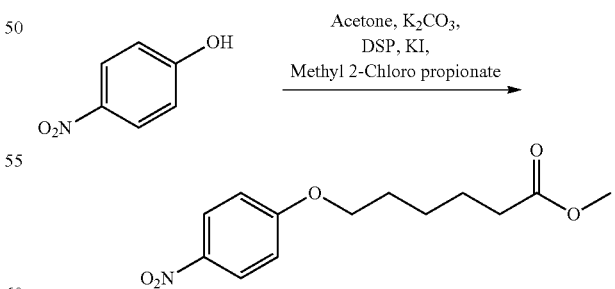

To a mixture of 4-nitrophenol (150 g), Potassium carbonate (600 g), sodium iodide (10 g) in anhydrous acetone (2.1 liter) was added methyl 6-bromohexanoate (156 g) and heated to reflux for 48 hours. Acetone was distilled and water (2 liter) was added. Crude 6-(4-nitrophenoxy)-hexanoic acid methyl ester was filtered, dried and recrystallised from a mixture of ethyl acetate and hexane (1:6) to obtain pure 6-(4-nitrophenoxy)-hexanoic acid methyl ester (130 g) as a white powder with a melting point of 84.5.5-86.6° C. The product was characterized by $^1$H NMR (CDCl$_3$) δ 1.56 (m, 2H, CH$_2$), 1.74 (m, 2H, CH$_2$), 1.90 (s, 2H, CH$_2$), 3.68 (s, 3H, Ester), 4.06 (t, 2H, CH$_2$), 6.92 (d, 2H, Ar), 8.20 (d, 2H, Ar).

Similarly, substitution of 4-nitrocyclohexanol for 4-nitrophenol provides the cyclohexane analog, according to procedures known to those skilled in the art.

Example 2

Synthesis of 6-(4-nitrophenoxy)-hexanoic acid

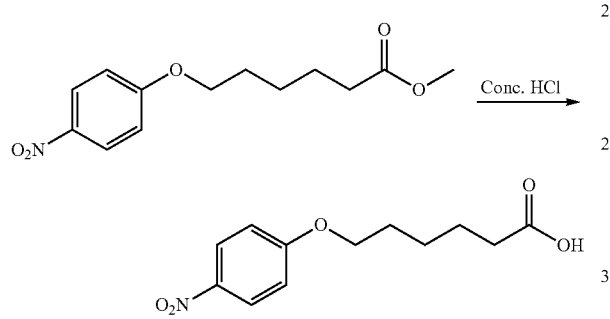

A mixture of 6-(4-nitrophenoxy)-hexanoic acid methyl ester (125 g) and concentrated hydrochloride acid (1.2 L) was refluxed for 16 hours. The reaction mixture cooled was to room temperature, filtered, dried and recrystallised from a mixture of ethyl acetate and hexane (1:6) to obtain pure 6-(4-nitrophenoxy)-hexanoic acid (95 g) as a white powder with a melting point of 104-107° C. The product was characterized by $^1$H NMR (CDCl$_3$) δ 1.60 (m, 2H, CH$_2$), 1.76 (m, 2H, CH$_2$), 1.90 (m, 2H, CH$_2$), 2.42 (t, 2H, CH$_2$), 4.04 (t, 2H$_2$, OCH$_2$), 6.96 (d, 2H, Ar), 8.20 (d, 2H, Ar).

Similarly, preparation of the non-aromatic (reduced) analog is achieved by substitution of the corresponding cyclohexane analog, according to procedures known to those skilled in the art.

Example 3

Synthesis of 6-(4-nitrophenoxy)-hexanoyl chloride

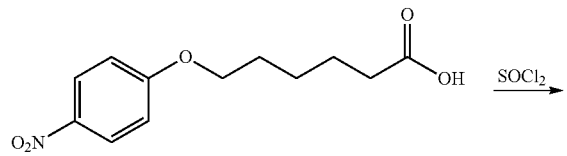

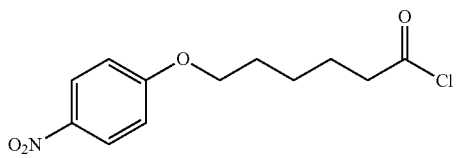

A mixture of 6-(4-nitrophenoxy)-hexanoic acid (20 g), thionyl chloride (40 ml) and dimethylformamide (0.5 ml) was refluxed for 5 hours. Excess thionyl chloride was distilled off under reduced pressure. Dry toluene (20 ml) added and solvent was removed under reduced pressure to obtain 6-(4-nitrophenoxy)-hexanoyl chloride (20 grams) as light yellow oil.

Similarly, preparation of the non-aromatic (reduced) analog is achieved by substitution of the corresponding cyclohexane analog, according to procedures known to those skilled in the art.

Example 4

Synthesis of 6-(4-nitrophenoxy)-hexanoic acid 4-nitrophenyl ester

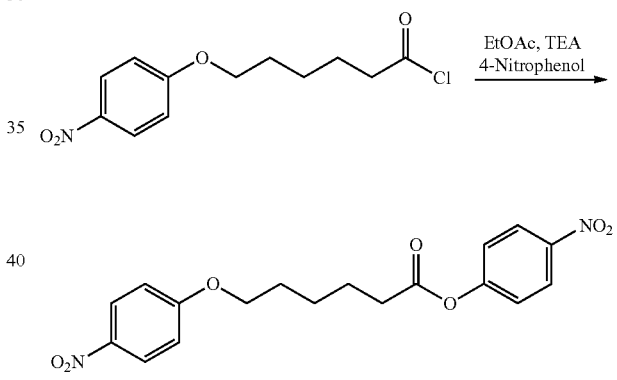

To a mixture of 4-nitrophenol (10.8 g), triethylamine (22 ml) in ethyl acetate (200 ml) at 0° C. was added 6-(4-nitrophenoxy)-hexanoyl chloride (20 g) dropwise, and the mixture was further stirred at room temperature for 16 hours. The reaction mixture was filtered to remove the salts, washed with 5% sodium bicarbonate, water and dried over anhydrous sodium sulphate. The solvent was distilled off under vacuum and the pure compound was precipitated by adding cold methanol. After filtration and drying, the compound was further recrystallized from a mixture of chloroform and methanol (1:1) to give pure 6-(4-nitrophenoxy)-hexanoic acid 4-nitrophenyl ester (15 grams) as white powder with a melting point of 73-76° C. The product was also characterized by $^1$H NMR (CDCl$_3$) δ 1.60 (m, 2H, CH$_2$), 1.85 (m, 6H, CH$_2$X2), 2.70 (t, 2H, CH$_2$), 4.10 (t, 2H, CH$_2$), 6.95 (d, 2H, Ar), 7.30 (d, 2H, Ar), 8.25 (m, 4H, Ar).

Similarly, preparation of the non-aromatic (reduced) analog is achieved by substitution of the corresponding cyclohexane analog, according to procedures known to those skilled in the art.

Example 5

Synthesis of 6-(4-aminophenoxy)-hexanoic acid 4-amino-phenyl ester

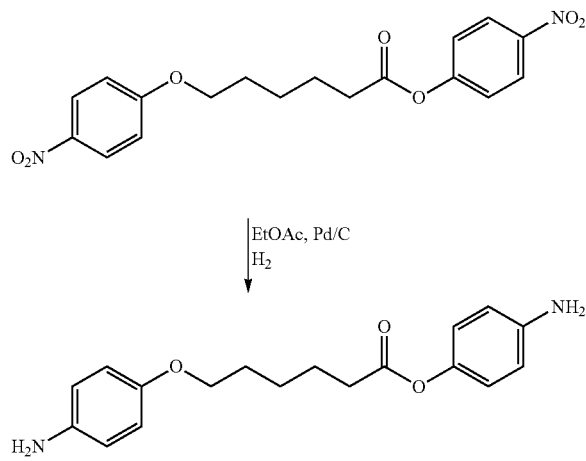

6-(4-nitrophenoxy)-hexanoic acid 4-nitrophenyl ester (20 g) was dissolved in ethyl acetate (150 ml) in a pressure vessel. Palladium on carbon (50% wet, 3 grams) was added as a catalyst and the mixture was stirred under an atmosphere of hydrogen (5 Kg) for 1 hour. The catalyst was removed by filtration and the solvent was distilled off under reduced pressure, and the residue was triturated with cold hexane, filtered, and dried to give pure 6-(4-aminophenoxy)-hexanoic acid 4-amino-phenyl ester (11 grams) as off-white powder with a melting point of 99-101° C. The product was characterized by $^1$H NMR (CDCl$_3$) δ 1.60 (m, 2H, CH$_2$), 1.85 (m, 6H, CH$_2$X2), 2.55 (t, 2H, CH$_2$), 3.50 (bs, 4H, NH$_2$), 3.90 (t, 2H, CH$_2$), 6.60 to 6.90 (m, 8H, Ar).

Similarly, preparation of the non-aromatic (reduced) analog is achieved by substitution of the corresponding cyclohexane analog, according to procedures known to those skilled in the art.

Hydrolysis 0.5 g of the above diamine was subjected to hydrolysis in 50 ml of pH 9.0 buffer at 100° C. The diamine was hydrolyzed in 3 hours.

Example 6

Synthesis of 6-(4-isocyanato-phenoxy)-hexanoic acid 4-isocyanato-phenyl ester

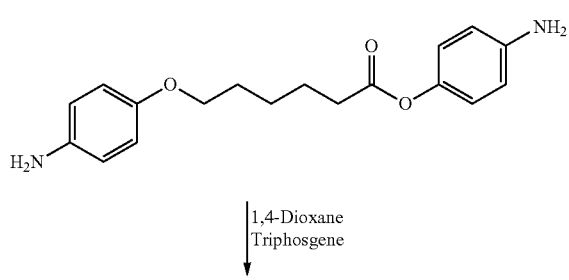

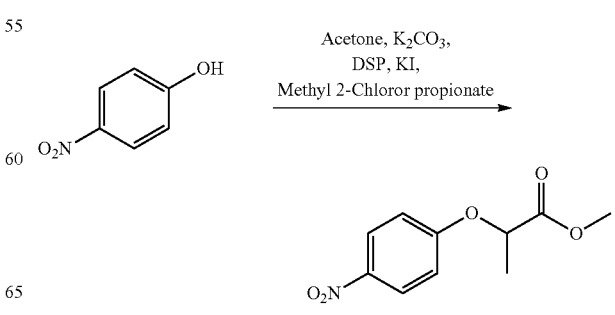

6-(4-Aminophenoxy)-hexanoic acid 4-amino-phenyl ester (10 g) was dissolved in dry 1,4-dioxane (160 ml) under nitrogen atmosphere, cooled to 10° C. and a solution of triphosgene (16 g) in dry 1,4-dioxane (40 ml) was added in one lot. The mixture was heated slowly to 80° C. and maintained at that temperature for 2 hours. The condenser was then arranged for distillation and solvent was removed by distillation at atmospheric pressure until the volume of the reaction mixture was reduced to approximately one third. Fresh dry 1,4-dioxane (50 ml) was added and distilled off under vacuum. The residue was re-evaporated two times from dry 1,4-dioxane to give crude 6-(4-isocyanato-phenoxy)-hexanoic acid 4-isocyanato-phenyl ester. Crude 6-(4-isocyanato-phenoxy)-hexanoic acid 4-isocyanato-phenyl ester was dissolved in toluene (50 ml), treated with charcoal (3 grams), filtered and the toluene was distilled off under vacuum. The resulting residue was triturated with cold hexane (75 ml) and filtered to give 6-(4-isocyanato-phenoxy)-hexanoic acid 4-isocyanato-phenyl ester (5 grams) as a white powder with a melting point of 62-64° C. The product was characterized by $^1$H NMR (CDCl$_3$) δ 1.60 (m, 2H, CH$_2$), 1.85 (m, 6H, CH$_2$X2), 2.70 (t, 2H, CH$_2$), 3.95 (t, 2H, CH$_2$), 6.80 (m, 2H, Ar), 7.10 (m, 6H, Ar).

Similarly, substitution of thiophosgene for triphosgene provides the isothiocyanate analog, according to procedures known to those skilled in the art. Also, preparation of the non-aromatic (reduced) analog is achieved by substitution of the corresponding cyclohexane analog, according to procedures known to those skilled in the art.

Hydrolysis of Diurethane

The diurethane of the above diisocyanate was prepared by reaction with methanol. 0.5 g of the diurethane was subjected to hydrolysis in 50 ml of pH 9.0 buffer at 50° C. The diamine was hydrolyzed in 4 hours.

In another preferred embodiment, monolactate diisocyanate compounds and the polymeric moieties obtained therefrom in Scheme 2, above, are prepared according to the steps described in examples 7-12.

Example 7

Synthesis of 2-(4-nitrophenoxy)-propionic acid methyl ester

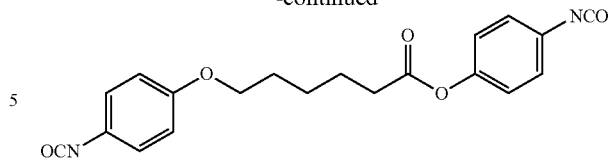

Into a mixture of 4-nitrophenol (90 g), potassium carbonate (268 g), potassium iodide (10 g) and disodium phosphate (10 g) in anhydrous acetone (900 ml) was added methyl 2-chloro propionate (95 g). The reaction mixture was stirred and refluxed for 24 hours. Acetone was distilled off and water (1.5 liter) was added to the reaction mixture. Crude 2-(4-nitrophenoxy)-propionic acid methyl ester was filtered, dried and recrystallised from methanol to obtain pure 2-(4-nitrophenoxy)-propionic acid methyl ester (80 g) as a white powder. The product was characterized by $^1$H NMR (CDCl$_3$) δ 1.70 (d, 3H, CH$_3$), 3.78 (s, 3H, Ester), 4.85 (q, 1H, CH), 6.92 (d, 2H, Ar), 8.20 (d, 2H, Ar). The product has a melting point of 83-84° C.

Similarly, preparation of the non-aromatic (reduced) analog is achieved by substitution of the corresponding cyclohexane analog, according to procedures known to those skilled in the art.

Example 8

Synthesis of 2-(4-nitrophenoxy)-propionic acid

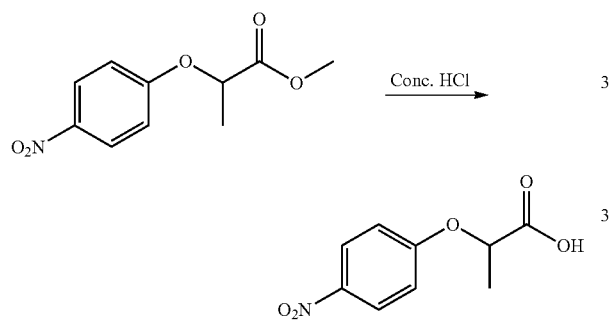

A mixture of 2-(4-nitrophenoxy)-propionic acid methyl ester (80 g) and concentrated hydrochloride acid (800 ml) was refluxed for 6 hours. The reaction mixture was cooled to room temperature. The product was filtered off and dried to obtain pure 2-(4-nitrophenoxy)-propionic acid (55 g) as a white powder with a melting point of 139-140° C.

Similarly, preparation of the non-aromatic (reduced) analog is achieved by substitution of the corresponding cyclohexane analog, according to procedures known to those skilled in the art.

Example 9

Synthesis of 2-(4-nitrophenoxy)-propionyl chloride

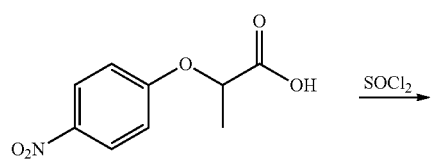

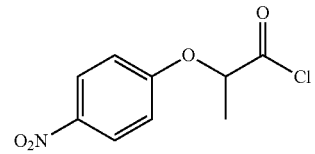

A mixture of 2-(4-nitrophenoxy)-propionic acid (40 g), thionyl chloride (80 ml) and dimethyl formamide (0.5 ml) was refluxed for 5 hours. Excess thionyl chloride was distilled off under reduced pressure. Dry toluene (20 ml) was added to the reaction mixture and solvent was removed under reduced pressure to obtain 2-(4-nitrophenoxy)-propionyl chloride (40 g) as light brown liquid.

Similarly, preparation of the non-aromatic (reduced) analog is achieved by substitution of the corresponding cyclohexane analog, according to procedures known to those skilled in the art.

Example 10

Synthesis of 2-(4-nitrophenoxy)-propionic acid-4-nitrophenyl ester

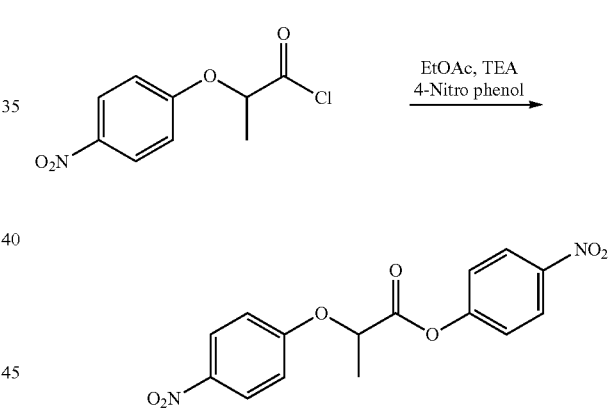

To a mixture of 4-nitrophenol (21.8 g) and triethylamine (33 ml) in ethyl acetate (360 ml) at 0° C. was added 2-(4-nitrophenoxy)-propionyl chloride (36 g) dropwise, and the mixture was further stirred at room temperature for 1 hour. The reaction mixture was filtered to remove the salts, washed with 5% sodium bicarbonate, followed by water, and the ethyl acetate layer was dried over anhydrous sodium sulphate. The solvent was distilled off under vacuum and the compound was precipitated by adding cold methanol. Filtration and drying gave pure 2-(4-nitrophenoxy)-propionic acid-4-nitrophenyl ester (35 g) as white powder. The product had a melting point of 136-139° C., with a purity of 99%. The product was characterized by $^1$H NMR (CDCl$_3$) δ 1.85 (d, 3H, CH$_3$), 5.15 (q, 1H, CH), 7.05 (d, 2H, Ar), 7.28 (d, 2H, Ar), 8.30 (m, 4H, Ar).

Similarly, preparation of the non-aromatic (reduced) analog is achieved by substitution of the corresponding cyclohexane analog, according to procedures known to those skilled in the art.

Example 11

Synthesis of 2-(4-aminophenoxy)-propionic acid 4-amino-phenyl ester

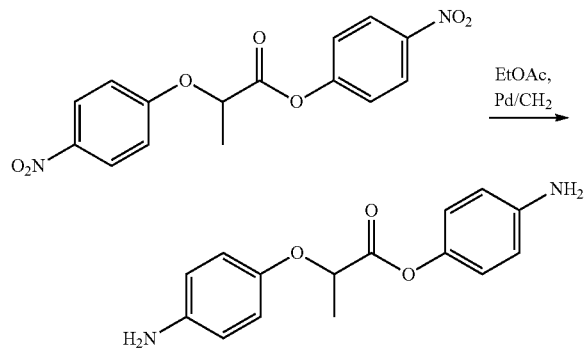

2-(4-nitrophenoxy)-propionic acid 4-nitrophenyl ester (30 grams, 90.28 mmoles) was dissolved in ethyl acetate (600 ml) in a pressure vessel, palladium on carbon (50% wet, 6 grams) was added and the mixture stirred under an atmosphere of Hydrogen (5 Kg) for 30 minutes. The catalyst was removed by filtration and the solvent distilled off under reduced pressure. The residue was triturated in cold diisopropyl ether, filtered and dried to give pure 2-(4-aminophenoxy)-propionic acid 4-amino-phenyl ester (15 grams) as off-white powder. The product has a melting point of 109-111° C. The product was characterized by $^1$H NMR (CDCl$_3$) δ 1.75 (d, 3H, CH$_3$), 3.50 (bs, 2H, NH$_2$), 4.90 (q, 1H, CH), 6.65 (m, 4H, Ar), 6.80 (m, 4H, Ar).

Similarly, preparation of the non-aromatic (reduced) analog is achieved by substitution of the corresponding cyclohexane analog, according to procedures known to those skilled in the art.

Hydrolysis of Diamine 0.5 g of the above diamine compound was subjected to hydrolysis studies in 50 ml of pH 9 buffer at 50° C. The diamine was completely hydrolyzed in 2 hours.

Example 12

Synthesis of 2-(4-isocyanato-phenoxy)-propionic acid 4-isocyanato-phenyl ester

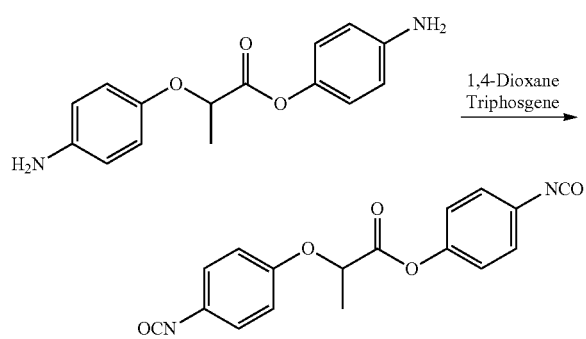

2-(4-Aminophenoxy)-propionic acid 4-amino-phenyl ester (6 g) was dissolved in dry 1,4-dioxane (100 ml) under nitrogen atmosphere. The reaction mixture was cooled to 10° C. and a solution of triphosgene (12 g) in dry 1,4-dioxane (30 ml) was added. The mixture was heated slowly to 100° C. and maintained at that temperature for 2 hours. The condenser was then arranged for distillation and solvent was removed by distillation under atmospheric pressure until the volume of the reaction mixture had been reduced to approximately one third. Fresh dry 1,4-dioxane (30 ml) was added. The solvent was distilled off under vacuum. The residue was re-evaporated two times from dry 1,4-dioxane to give crude 2-(4-isocyanato-phenoxy)-propionic acid 4-isocyanato-phenyl ester. Crude 2-(4-isocyanato-phenoxy)-propionic acid 4-isocyanato-phenyl ester was dissolved in toluene (40 ml) and treated with charcoal (1 g). The solution was filtered off and the toluene was distilled off under vacuum to give 2-(4-isocyanato-phenoxy)-propionic acid 4-isocyanato-phenyl ester (5 g) as a light yellow syrup. The product was characterized by $^1$H NMR (CDCl$_3$) δ 1.75 (d, 3H, CH$_3$), 4.95 (q, 1H, CH), 6.80 to 7.10 (m, 8H, Ar).

Similarly, substitution of thiophosgene for triphosgene provides the isothiocyanate analog. Also, preparation of the non-aromatic (reduced) analog is achieved by substitution of the corresponding cyclohexane analog, according to procedures known to those skilled in the art.

Hydrolysis of Diurethane

The diurethane of the above diisocyanate was prepared by reaction with methanol. 0.5 g of the diurethane compound (a white powder having a melting point of 145-147° C.) was subjected to hydrolysis studies in 50 ml of pH 9 buffer at 50° C. for 4 hours, followed by four hours at 80° C. The diurethane was completely hydrolyzed during the course of the 8 hour period.

In yet another embodiment, diethylene glycol glycolate diisocyanate phenols; (4-isocyanato-Phenoxy)-Acetic acid 2-[2-(4-isocyanato-Phenoxy)-acetoxy]-ethoxy)-ethyl ester, are described in Scheme 3 and synthesized according to the steps of examples 13-16, as follows.

Example 13

Synthesis of chloroacetic acid 2-[2-(2-chloro-acetoxy)-ethoxy]-ethyl ester

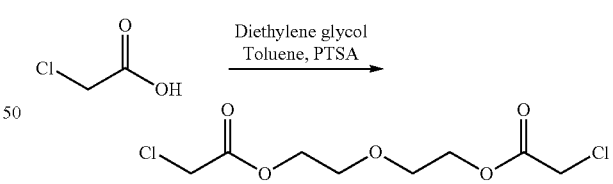

In a 10-liter 4-neck round bottom flask equipped with a mechanical stirrer and Dean-Stark apparatus was added a solution of diethylene glycol (500 g), chloro acetic acid (980 g) and para-toluene sulphonic acid (25 g) in toluene (2.5 L). The solution was refluxed with stirring and azeotropic removal of water for 5 hours, and then cooled to room temperature. The toluene layer was washed with 5% sodium bicarbonate solution (3×1000 ml) and water (3 L). The toluene layer was dried over anhydrous sodium sulphate, filtered, and distilled to obtain chloro-acetic acid 2-[2-(2-chloro-acetoxy)-ethoxy]-ethyl ester (1.1 Kg) as light yellow oil. The product was characterized by $^1$H NMR (CDCl$_3$) δ 3.75 (t, 2H, CH$_2$), 4.12 (s, 2H, CH$_2$), 4.36 (t, 2H, CH$_2$)

Example 14

Synthesis of (4-nitrophenoxy)-acetic acid 2-{2-[2-(4-nitrophenoxy)-acetoxy]-ethoxy}ethyl ester

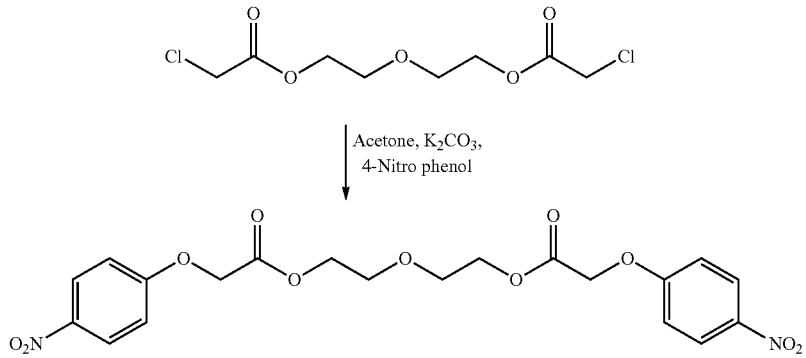

To a mixture of 4-nitrophenol (966 g), potassium carbonate (4.26 Kg), sodium iodide (60 g), and disodium phosphate (60 g) in acetone (10 L) was added chloro-acetic acid 2-[2-(2-chloro-acetoxy)-ethoxy]-ethyl ester (1 Kg) and the mixture was stirred at reflux for 8 hours. Acetone was distilled off and cold water (250 ml) was added. The crude product was filtered off and slurried in methanol (10 L), re-filtered and dried to give (4-nitrophenoxy)-acetic acid 2-{2-[2-(4-nitrophenoxy)-acetoxy]-ethoxy}-ethyl ester (1450 grams) as a white powder with a melting point of 73-75° C. The product was characterized by $^1$H NMR (CDCl$_3$) δ 3.62 (t, 2H, CH$_2$), 4.40 (t, 2H, CH$_2$), 4.78 (s, 2H, CH$_2$), 6.95 (d, 2H, Ar), 8.15 (d, 2H, Ar).

Similarly, substitution of 4-nitrocyclohexanol for 4-nitrophenol provides the cyclohexane analog, according to procedures known to those skilled in the art.

Example 15

Synthesis of (4-aminophenoxy)-acetic acid 2-{2-[2-(4-aminophenoxy)-acetoxy]-ethoxy}-ethyl ester (4-nitrophenoxy)-acetic acid 2-{2-[2-(4-nitrophenoxy)-acetoxy]-ethoxy}-ethyl ester (600 g) was dissolved in dimethylformamide (1.8 l) in a pressure vessel. Raney Nickel (800 grams) added and the mixture was stirred under an atmosphere of hydrogen (20 Kg) for 3 hours. The catalyst was removed by filtration and the solution was added to cold water to precipitate the crude product. The product was filtered off, slurried in methanol and re-filtered. The compound was dried to give pure (4-aminophenoxy)-acetic acid 2-{2-[2-(4-aminophenoxy)-acetoxy]-ethoxy}-ethyl ester (428 grams) as off-white powder with a melting point of 95-97° C. The product was characterized by $^1$H NMR (CDCl$_3$) δ 3.10 (bs, 2H, NH$_2$), 3.70 (t, 2H, CH$_2$), 4.35 (t, 2H, CH$_2$), 4.55 (s, 2H, CH$_2$), 6.60 (d, 2H, Ar), 6.75 (d, 2H, Ar).

Similarly, preparation of the non-aromatic (reduced) analog is achieved by substitution of the corresponding cyclohexane analog, according to procedures known to those skilled in the art.

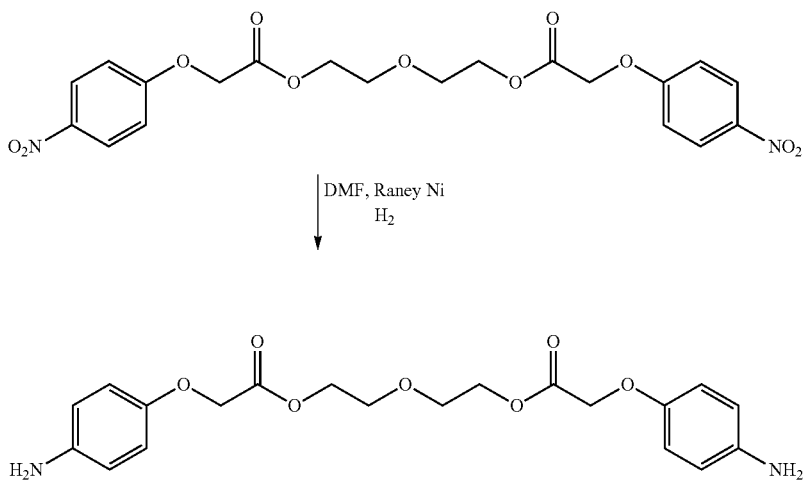

Hydrolysis Data of Diamine:

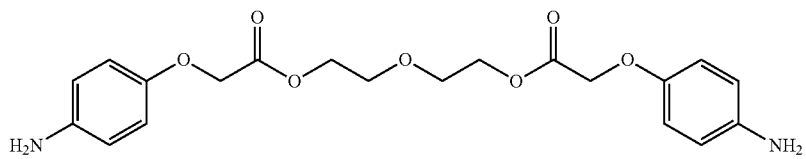

0.5 g of the above diamine was subjected to hydrolysis in 50 ml of pH 9.0 buffer at 50° C. for 15 hours and then at 100° C. for 2 hours. The diamine was completely hydrolyzed.

Example 16

Synthesis of (4-isocyanato-phenoxy)-acetic acid 2-{2-[2-(4-isocyanato-phenoxy)-acetoxy]-ethoxy}-ethyl ester

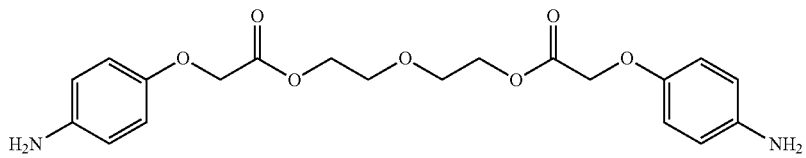 [SMILES: Nc1ccc(OCC(=O)OCCOCCOC(=O)COc2ccc(N)cc2)cc1]

1,4-Dioxane
Triphosgene

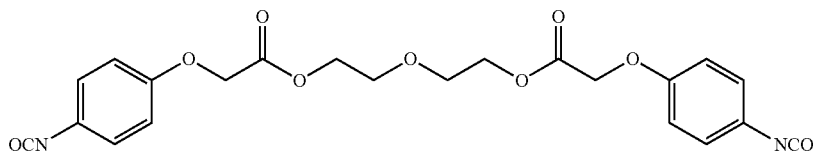

(4-Aminophenoxy)-acetic acid 2-{2-[2-(4-aminophenoxy)-acetoxy]-ethoxy}-ethyl ester (200 grams, 495 mmoles) was dissolved in dry 1,4-dioxane (2000 ml) under nitrogen atmosphere and cooled to below 10° C. A solution of triphosgene (250 grams, 842.45 mmoles) in dry 1,4-dioxane (600 ml) was added. The mixture was heated slowly to 80° C. and maintained at that temperature for 2 hours. The condenser was then arranged for distillation and the solvent was removed by distillation at atmospheric pressure until the volume of the reaction mixture had been reduced to approximately one third. Fresh dry 1,4-dioxane (600 ml) was added and distilled off under vacuum. The residue was re-evaporated two times from dry 1,4-dioxane (1.2 L), then dry toluene (600 ml) and charcoal (20 g) were added. The solution was filtered hot, and toluene was distilled off under vacuum to give pure (4-isocyanato-phenoxy)-acetic acid 2-{2-[2-(4-isocyanato-phenoxy)-acetoxy]-ethoxy}-ethyl ester (4.5 g) as a light yellow syrup. The product was characterized by $^1$H NMR (CDCl$_3$) δ 3.65 (t, 2H, CH$_2$), 4.35 (t, 2H, CH$_2$), 4.65 (s, 2H, CH$_2$), 6.75 (d, 2H, Ar), 7.00 (d, 2H, Ar).

Similarly, substitution of thiophosgene for triphosgene provides the isothiocyanate analog. Also, preparation of the non-aromatic (reduced) analog is achieved by substitution of the corresponding cyclohexane analog, according to procedures known to those skilled in the art.

Hydrolysis Data of Diurethane:

The diurethane of the above diisocyanate was prepared by reaction with methanol.

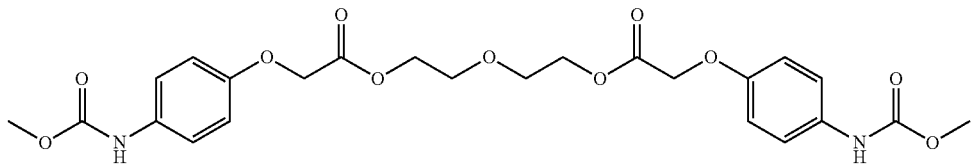

5 grams of the diurethane was hydrolyzed in pH 9 buffer at 100° C. for 2 hours, and after the hydrolysis a compound was isolated (1.5 grams), as a white powder with a melting point of 163-167° C., whose NMR spectrum indicated the formation of the following product, clearly resulting from the hydrolysis of the diethylene glycol linkage: $^1$H NMR (CDCl$_3$) δ 3.75 (s, 3H, CH$_3$), 4.65 (s, 2H, CH$_2$), 6.55 (bs, 1H, NH), 6.90 (d, 2H, Ar), 7.30 (d, 2H, Ar).

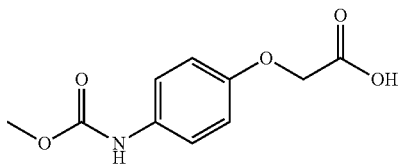 [SMILES: COC(=O)Nc1ccc(OCC(=O)O)cc1]

In another embodiment, diethylene glycol dilactate diisocyanate phenols; (4-isocyanato-phenoxy)-propionic acid 2-{2-[2-(4-isocyanato-phenoxy)-propionyloxy]-ethoxy}-ethyl ester; are described in the Scheme 4 and synthesized according to the following steps of examples 17-21.

Example 17

Synthesis of 2-chloropropionic acid 2-[2-(2-chloropropionyloxy)-ethoxy]-ethyl ester

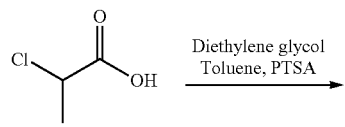

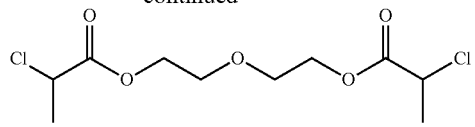

In a 20 L glass reactor equipped with a Dean-Stark apparatus was added a solution of diethylene glycol (1500 g), 2-chloropropionic acid (3200 g) and para-toluene sulphonic acid (50 g) in toluene (5 L). The reaction mixture was refluxed for 5 hours with azeotropic removal of water, and then cooled to room temperature. The toluene layer was washed with 5% sodium bicarbonate solution (4500 ml) and water (4 L). The toluene layer was dried over anhydrous anhydrous sodium sulphate, and distilled to obtain 2-chloropropionic acid 2-[2-(2-chloropropionyloxy)-ethoxy]-ethyl ester (3.3 Kg) as light yellow oil. The product was characterized by $^1$H NMR (CDCl$_3$) δ 1.65 (d, 3H, CH$_3$), 3.75 (t, 2H, CH$_2$), 4.40 (t, 2H, CH$_2$), 4.48 (q, 1H, CH)

Example 18

Synthesis of (4-nitrophenoxy)-propionic acid 2-{2-[2-(4-nitrophenoxy)-propionyloxy]-ethoxy}-ethyl ester

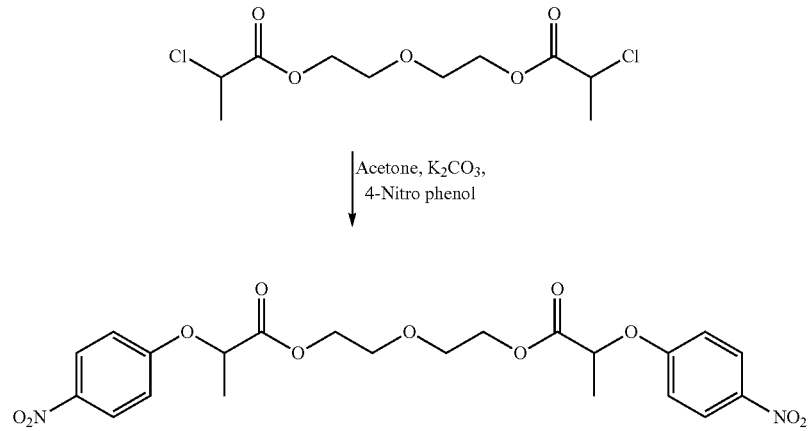

To a mixture of 4-nitrophenol (2.6 Kg), potassium carbonate (11.5 Kg), sodium iodide (100 g), and disodium phosphate (100 g) in acetone (30 L) was added 2-chloropropionic acid 2-[2-(2-chloro-propionyloxy)-ethoxy]-ethyl ester (3 Kg). The reaction mixture was refluxed with stirring for 48 hours. The acetone was distilled off and cold water (25 L) was added. The crude product was extracted into chloroform (15 L) and the chloroform extract was dried over anhydrous sodium sulphate. Chloroform was distilled off and the final product was precipitated from methanol. The solid was collected by filtration, dried and recrystallised to give (4-nitrophenoxy)-propionic acid 2-{2-[2-(4-nitrophenoxy)-propionyloxy]-ethoxy}-ethyl ester (745 grams) as a white powder. The product was characterized by $^1$H NMR (CDCl$_3$) δ 1.65 (d, 3H, CH$_3$), 3.65 (t, 2H, CH$_2$), 4.30 (t, 2H, CH$_2$), 4.85 (q, 1H, CH), 6.90 (d, 2H, Ar), 8.20 (d, 2H, Ar).

Similarly, substitution of 4-nitrocyclohexanol for 4-nitrophenol provides the cyclohexane analog, according to procedures known to those skilled in the art.

Example 19

Synthesis of (4-aminophenoxy)-propionic acid 2-{2-[2-(4-aminophenoxy)-propionyloxy]-ethoxy}-ethyl ester

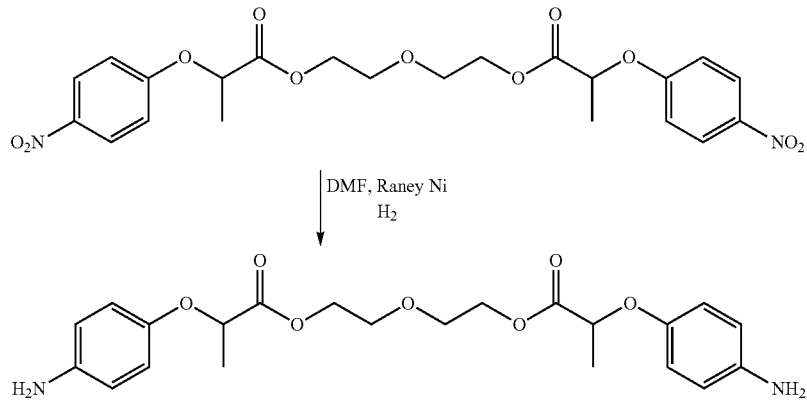

(4-Nitrophenoxy)-propionic acid 2-{2-[2-(4-nitrophenoxy)-propionyloxy]-ethoxy}-ethyl ester (300 g) was dissolved in ethyl acetate (1.5 L) in a pressure vessel. Raney Nickel catalyst (290 g) was added and the mixture was stirred under an atmosphere of hydrogen (10 Kg) for 4 hour. The catalyst was removed by filtration and the solvent was distilled off under reduced pressure to obtain pure (4-aminophenoxy)-propionic acid 2-{2-[2-(4-aminophenoxy)-propionyloxy]-ethoxy}-ethyl ester (254 g) as a light yellow syrup. The product was characterized by $^1$H NMR (CDCl$_3$) δ 1.60 (d, 3H, CH$_3$), 3.20 (bs, 2H, NH$_2$), 3.60 (t, 2H, CH$_2$), 4.25 (t, 2H, CH$_2$), 4.65 (q, 1H, CH), 6.60 (d, 2H, Ar), 6.75 (d, 2H, Ar).

Similarly, preparation of the non-aromatic (reduced) analog is achieved by substitution of the corresponding cyclohexane analog, according to procedures known to those skilled in the art.

Hydrolysis Data of Diamine:

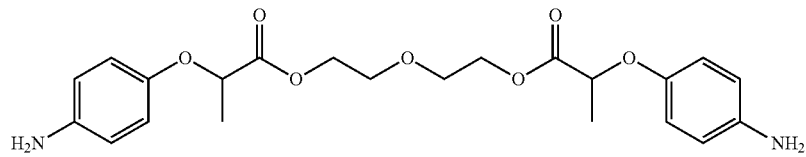 [SMILES: CC(Oc1ccc(N)cc1)C(=O)OCCOCCOC(=O)C(C)Oc1ccc(N)cc1]

0.5 g of the above diamine was subjected to hydrolysis in 50 ml of pH 9.0 buffer at 50° C. The diamine was hydrolyzed in 1.5 hours

Example 20

Synthesis of (4-isocyanato-phenoxy)-propionic acid 2-{2-[2-(4-isocyanato-phenoxy)-propionyloxy]-ethoxy}-ethyl ester

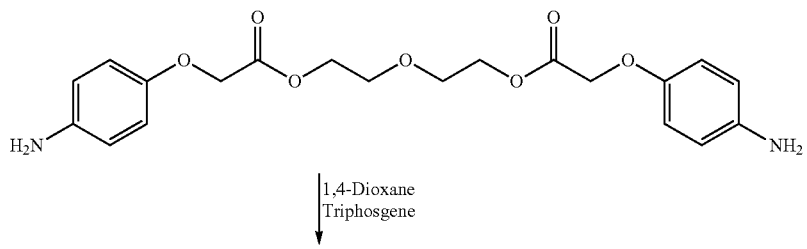

1,4-Dioxane
Triphosgene

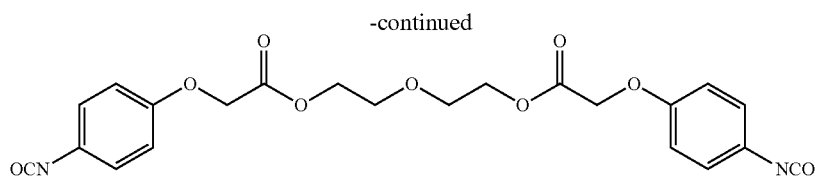

(4-Aminophenoxy)-propionic acid 2-{2-[2-(4-aminophenoxy)-propionyloxy]-ethoxy}-ethyl ester (217 g) was dissolved in dry 1,4-dioxane (2 L) under nitrogen atmosphere. The reaction mixture was cooled down to below 10° C. A solution of triphosgene (253 g) in dry 1,4-dioxane (600 ml) was added. The mixture was heated slowly to 80° C. and maintained at that temperature for 2 hours. The condenser was then arranged for distillation and solvent removed by distillation under atmospheric pressure until the volume of the reaction mixture had been reduced to approximately one third. Fresh dry 1,4-dioxane (600 ml) was added. Solvents were distilled off under vacuum. The residue was re-evaporated two times from dry 1,4-dioxane (1200 ml). Dry toluene (600 ml) and charcoal (50 g) was added. The solution was filtered hot and toluene was distilled off under vacuum to give pure (4-isocyanato-phenoxy)-propionic acid 2-{2-[2-(4-isocyanato-phenoxy)-propionyloxy]-ethoxy}-ethyl ester (165 g) as a light yellow syrup. The product was characterized by $^1$H NMR (CDCl$_3$) δ 1.65 (d, 3H, CH$_3$), 3.65 (t, 2H, CH$_2$), 4.30 (t, 2H, CH$_2$), 4.75 (q, 1H, CH), 6.80 (d, 2H, Ar), 7.00 (d, 2H, Ar).

Similarly, substitution of thiophosgene for triphosgene provides the isothiocyanate analog. Also, preparation of the non-aromatic (reduced) analog is achieved by substitution of the corresponding cyclohexane analog, according to procedures known to those skilled in the art.

Hydrolysis Data of Diurethane:

The diurethane of the above diisocyanate was prepared by reaction with methanol.

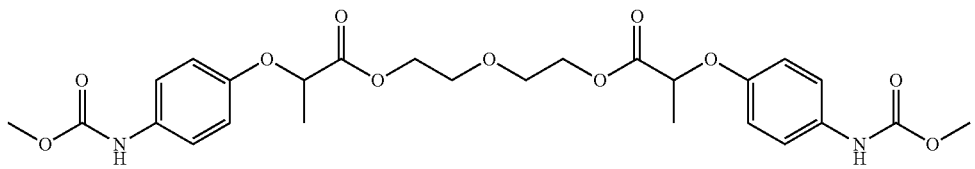

0.5 g of the diurethane was subjected to hydrolysis in 50 ml of pH 9.0 buffer at 50° C. The diurethane was hydrolyzed in 7 hours.

In yet another embodiment, diethylene glycol caprolactone diisocyanate phenol described in the Scheme 5 is synthesized according to the following steps of examples 21-26.

Example 21

Synthesis of 6-bromohexanoic acid 2-[2-(6-bromohexanoyloxy)-ethoxy]-ethyl ester

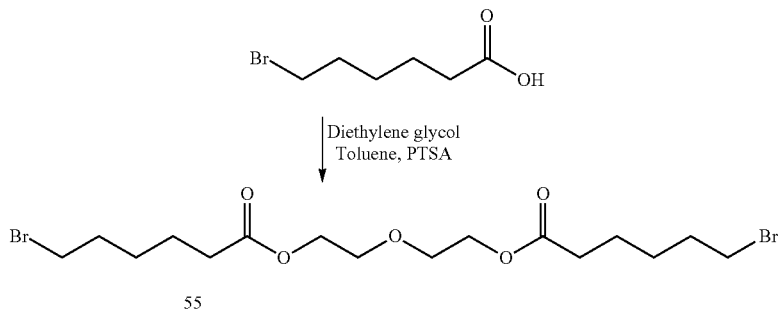

Into a 3-liter 4-neck round bottom flask equipped with a mechanical stirrer was added a solution of diethylene glycol (100 g), 6-Bromo hexanoic acid (386 g) and para-toluene sulphonic acid (5 g) in toluene (1000 ml). The solution was refluxed for 3 hours in a Dean-Stark apparatus with azeotropic removal of water. The solution was cooled to room temperature and the toluene layer was washed with water (600 ml), 5% sodium bicarbonate solution (1500 ml) and water (600 ml). The toluene layer was dried over anhydrous sodium sulphate, filtered and distilled to obtain 6-bromohexanoic acid 2-[2-(6-bromohexanoyloxy)-ethoxy]-ethyl ester (400 g) as light yellow oil.

Example 22

Synthesis of 6-(4-nitrophenoxy)-hexanoic acid 2-{2-[6-(4-nitrophenoxy)-hexanoyloxy]-ethoxy}-ethyl ester

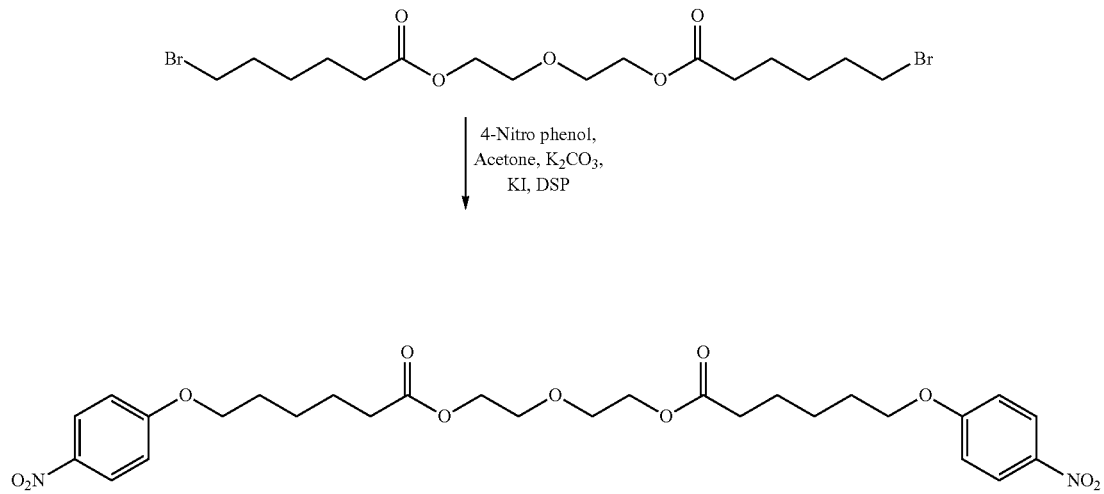

Into a mixture of 4-nitrophenol (60.5 g), potassium carbonate (180 g), potassium iodide (15 g), and disodium phosphate (15 g) in acetone (1000 ml) was added 6-bromohexanoic acid 2-[2-(6-bromohexanoyloxy)-ethoxy]-ethyl ester (100 g). The solution was stirred at reflux for 24 hours. The acetone layer was distilled off and cold water (250 ml) was added. The crude product was extracted into chloroform and the chloroform extract was washed with 5% sodium bicarbonate solution (800 ml) followed by water (600 ml). The chloroform layer was dried over anhydrous sodium sulphate and distilled, and the final product was precipitated by adding diisopropyl ether. The crude product was isolated by filtration and drying. The final product was recrystallized using a mixture of ethyl acetate and diisopropyl ether (1:3) to give pure 6-(4-nitrophenoxy)-hexanoic acid 2-{2-[6-(4-nitrophenoxy)-hexanoyloxy]-ethoxy}-ethyl ester (100 grams) as a white powder. The product was characterized by $^1$H NMR (CDCl$_3$) δ 1.50 (m, 2H, CH$_2$), 1.70 (m, 2H, CH$_2$), 1.82 (m, 2H, CH$_2$), 2.38 (t, 2H, CH$_2$), 3.74 (t, 2H, CH$_2$), 4.08 (t, 2H, CH$_2$), 4.26 (t, 2H, CH$_2$), 6.92 (d, 2H, Ar), 8.20 (d, 2H, Ar). The product has a melting point of 60-62° C.

Similarly, substitution of 4-nitrocyclohexanol for 4-nitrophenol provides the cyclohexane analog, according to procedures known to those skilled in the art.

Example 23

Synthesis of 6-(4-aminophenoxy)-hexanoic acid 2-{2-[6-(4-aminophenoxy)-hexanoyloxy]-ethoxy}-ethyl ester

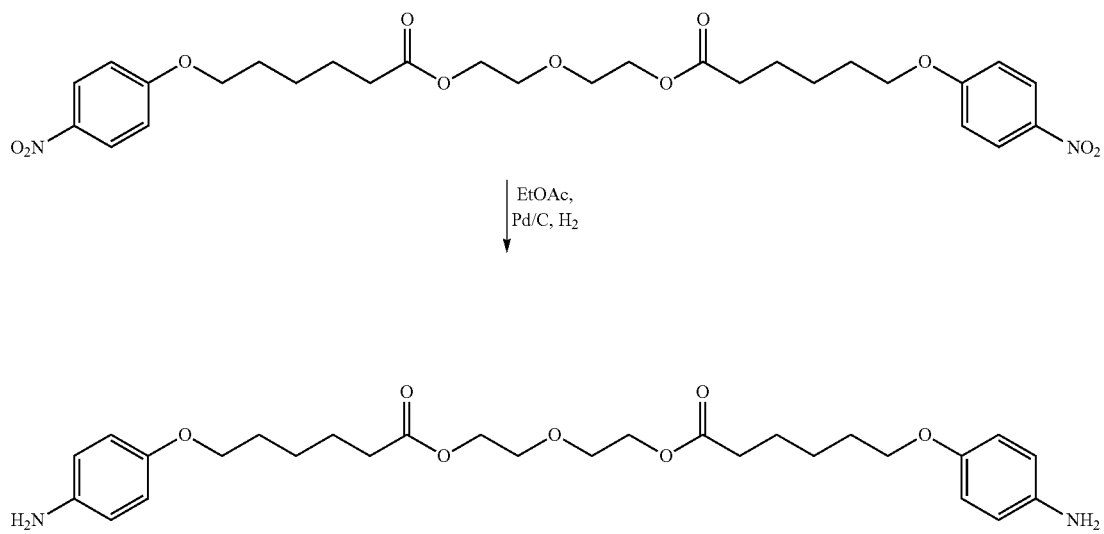

6-(4-Nitrophenoxy)-hexanoic acid 2-{2-[6-(4-nitrophenoxy)-hexanoyloxy]-ethoxy}-ethyl ester (12 g) was dissolved in ethyl acetate (200 ml) in a pressure vessel. 5% Palladium on carbon (50% wet, 3 g) was added and the mixture was stirred under an atmosphere of hydrogen (5 Kg) for 1.5 hours. The catalyst was removed by filtration, and the solvent was distilled off under reduced pressure to obtain the crude product which self crystallized over a period of time in the cold. The final product was slurried in diethyl ether, filtered and dried to give pure 6-(4-aminophenoxy)-hexanoic acid 2-{2-[6-(4-aminophenoxy)-hexanoyloxy]-ethoxy}-ethyl ester (6 g) as off-white powder. The final product was characterized by $^1$H NMR (CDCl$_3$) δ 1.52 (m, 2H, CH$_2$), 1.65 (m, 4H, 2×CH$_2$), 2.37 (t, 2H, CH$_2$), 3.20 (bs, 2H, NH$_2$), 3.70 (t, 2H, CH$_2$), 3.88 (t, 2H, CH$_2$), 4.24 (t, 2H, CH$_2$), 6.64 (d, 2H, Ar), 6.74 (d, 2H, Ar). The product has a melting point of 56-58° C.

Similarly, preparation of the non-aromatic (reduced) analog is achieved by substitution of the corresponding cyclohexane analog, according to procedures known to those skilled in the art.

Hydrolysis Data of Diamine:

6-(4-Aminophenoxy)-hexanoic acid 2-{2-[6-(4-aminophenoxy)-hexanoyloxy]-ethoxy}-ethyl ester (5 g) was dissolved in dry 1,4-dioxane (80 ml) under nitrogen atmosphere. The solution was cooled to below 10° C. A solution of triphosgene (4.8 g) in dry 1,4-dioxane (20 ml) was added. The mixture was heated slowly to 80° C. and maintained at that temperature for 2 hours. The condenser was then arranged for distillation and the solvent was removed by distillation at atmospheric pressure until the volume of the reaction mixture had been reduced to approximately one third. Fresh dry 1,4-dioxane (25 ml) was added. The solvents were distilled off under vacuum. The residue was re-evaporated from dry 1,4-dioxane (50 ml) and dry toluene (30 ml) and charcoal (2 gram) was added. The solution was filtered hot. The toluene was distilled off under vacuum to give pure 6-(4-isocyanatophenoxy)-hexanoic acid 2-{2-[6-(4-isocyanatophenoxy)-hexanoyloxy]-ethoxy}-ethyl ester (4.5 g) as a light yellow oil. The product was characterized by $^1$H NMR (CDCl$_3$) δ 1.48 (m, 2H, CH$_2$), 1.68 (m, 2H, CH$_2$), 1.78 (m, 2H, CH$_2$), 2.37 (t, 2H, CH$_2$), 3.68 (t, 2H, CH$_2$), 3.92 (t, 2H, CH$_2$), 4.24 (t, 2H, CH$_2$), 6.78 (d, 2H, Ar), 6.97 (d, 2H, Ar).

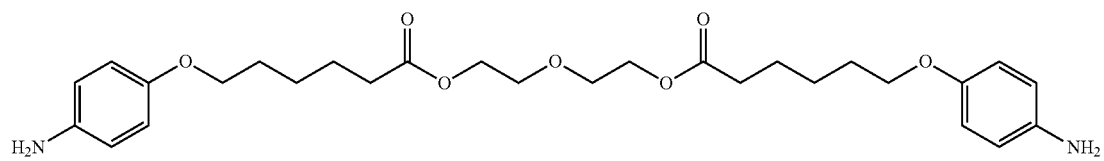 [SMILES: Nc1ccc(OCCCCCC(=O)OCCOCCOC(=O)CCCCCOc2ccc(N)cc2)cc1]

0.5 g of the above diamine was subjected to hydrolysis in 50 ml of pH 9.0 buffer at 100° C. The diamine was hydrolyzed in 2 hours.

Example 24

Synthesis of 6-(4-isocyanato-phenoxy)-hexanoic acid 2-{2-[6-(4-isocyanato-phenoxy)-hexanoyloxy]-ethoxy}-ethyl ester Similarly, substitution of thiophosgene for triphosgene provides the isothiocyanate analog. Also, preparation of the non-aromatic (reduced) analog is achieved by substitution of the corresponding cyclohexane analog, according to procedures known to those skilled in the art.

Hydrolysis Data of Diurethane:

The diurethane of the above diisocyanate was prepared by reaction with methanol.

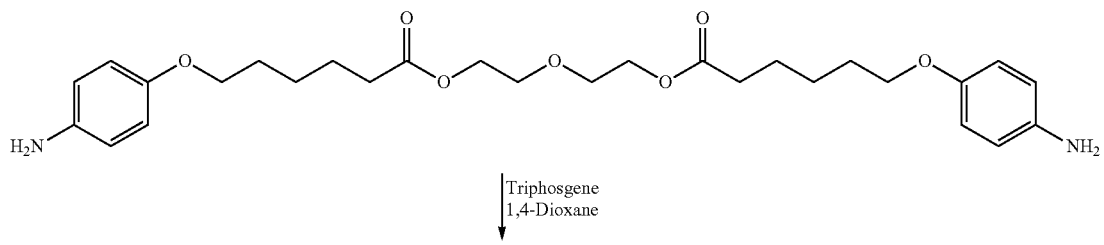

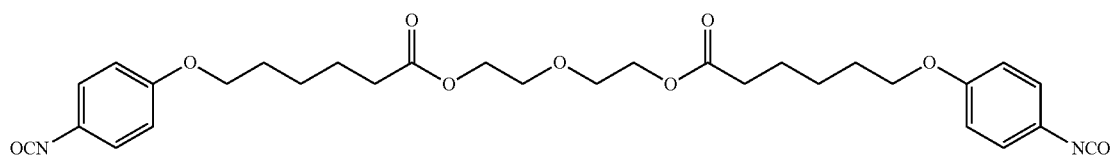

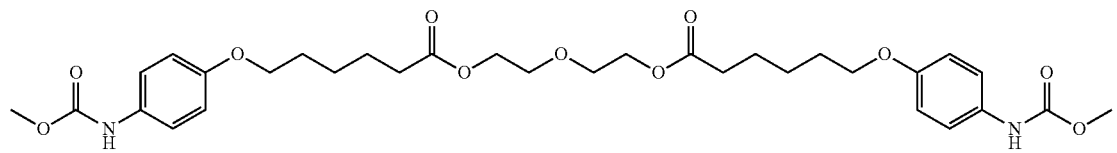

0.5 g of diurethane was subjected to hydrolysis in 50 ml of pH 9.0 buffer at 100° C. The diamine was hydrolyzed in 8 hours.

In yet another embodiment, diethylene glycol caprolactone diisocyanate benzoic acid described in the Scheme 6 is synthesized according to the following steps of examples 25-28.

Example 25

Synthesis of 6-bromohexanoic acid 2-[2-(6-bromohexanoyloxy)-ethoxy]-ethyl ester

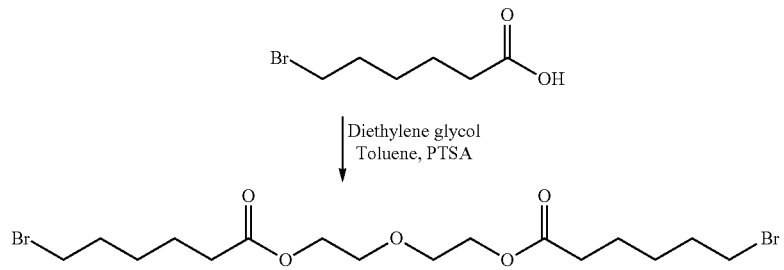

Into a 3-liter 4-neck round bottom flask equipped with a mechanical stirrer was added a solution of diethylene glycol (100 g), 6-bromo hexanoic acid (386 g) and para-toluene sulphonic acid (5 g) in toluene (1000 ml). The solution was refluxed for 3 hours using a Dean-Stark apparatus with azeotropic removal of water. The solution was cooled to room temperature. The toluene layer was washed with 5% sodium bicarbonate solution (1500 ml) and water (1000 ml). The solution was dried over anhydrous sodium sulphate and distilled to obtain 6-bromohexanoic acid 2-[2-(6-bromohexanoyloxy)-ethoxy]-ethyl ester (400 g) as light yellow oil.

Example 26

Synthesis of Dinitro Compound

Into a mixture of 4-nitrobenzoic acid (44 g) and triethylamine (76 ml) in dimethyl formamide (250 ml) was added 6-bromohexanoic acid 2-[2-(6-bromohexanoyloxy)-ethoxy]-ethyl ester (50 g), and the mixture was stirred at room temperature for 24 hours. The reaction mixture was poured onto cold water (1000 ml). The crude product was extracted into chloroform, and the chloroform extract was washed with 5% sodium bicarbonate solution (800 ml) followed by water (600 ml). The chloroform layer was dried over anhydrous sodium sulphate. Chloroform was distilled off and the crude product was purified by column chromatography using hexane and ethyl acetate (80:20) as eluent to give pure dinitro compound (28 grams) as light yellow syrup. The product was characterized by $^1$H NMR (CDCl$_3$) δ 1.50 (m, 2H, CH$_2$), 1.70 (m, 2H, CH$_2$), 1.82 (m, 2H, CH$_2$), 2.38 (t, 2H, CH$_2$), 3.70 (t, 2H, CH$_2$), 4.24 (t, 2H, CH$_2$), 4.38 (t, 2H, CH$_2$), 8.20 (d, 2H, Ar), 8.28 (d, 2H, Ar).

Similarly, substitution of 4-nitrocyclohexanol for 4-nitrophenol provides the cyclohexane analog, according to procedures known to those skilled in the art.

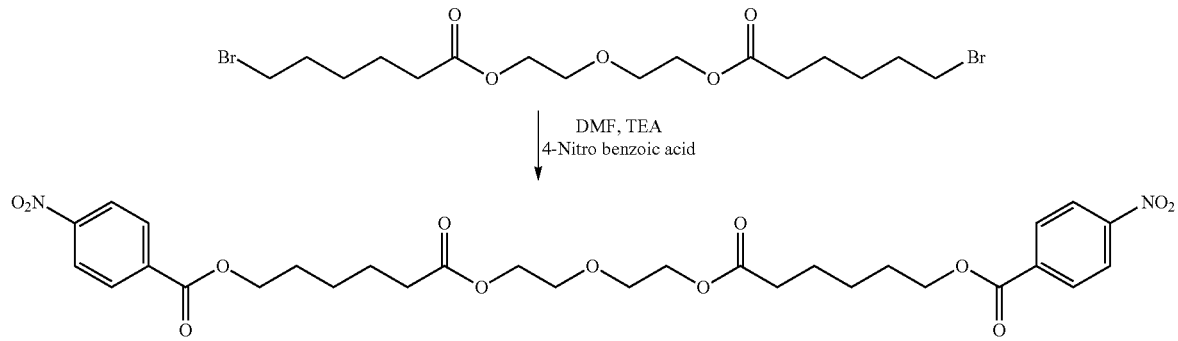

Example 27

Synthesis of Diamine

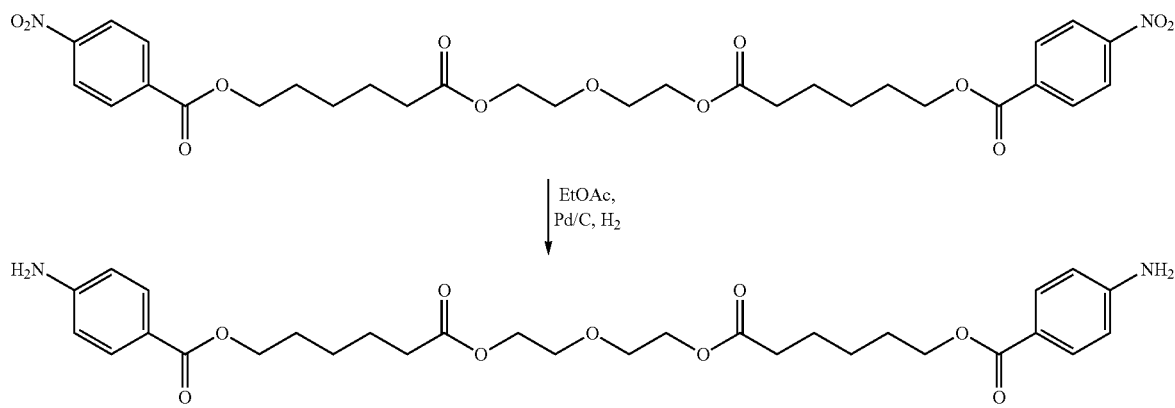

Dinitro compound (28 g) was dissolved in ethyl acetate (200 ml) in a pressure vessel. 5% Palladium on carbon (50% wet, 5 g) was added as catalyst and the mixture was stirred under an atmosphere of hydrogen (5 Kg) for 3 hours. The catalyst was removed by filtration and ethyl acetate was distilled off under reduced pressure to obtain the pure diamine compound (24 g) as light yellow thick syrup. The product was characterized by $^1$H NMR (CDCl$_3$) δ 1.48 (m, 2H, CH$_2$), 1.70 (m, 4H, 2×CH$_2$), 2.35 (t, 2H, CH$_2$), 3.65 (t, 2H, CH$_2$), 4.10 (bs, 2H, NH$_2$), 4.25 (m, 4H, 2×CH$_2$), 6.60 (d, 2H, Ar), 7.85 (d, 2H, Ar).

Similarly, preparation of the non-aromatic (reduced) analog is achieved by substitution of the corresponding cyclohexane analog, according to procedures known to those skilled in the art.

Hydrolysis Data of Diamine:

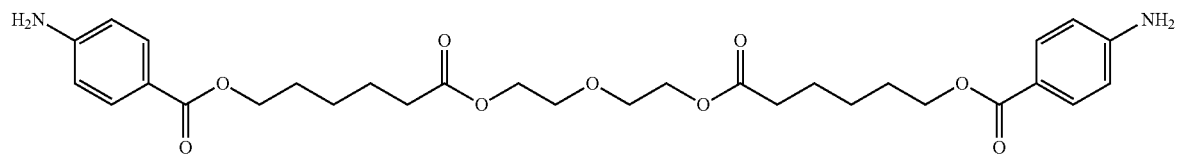 [SMILES: Nc1ccc(C(=O)OCCCCCC(=O)OCCOCCOC(=O)CCCCCOC(=O)c2ccc(N)cc2)cc1]

0.5 g of the above diamine compound was subjected to hydrolysis studies in 50 ml of pH 9 buffer at 100° C. The diamine was completely hydrolyzed in 3 hours.

Example 28

Synthesis of Diisocyanate

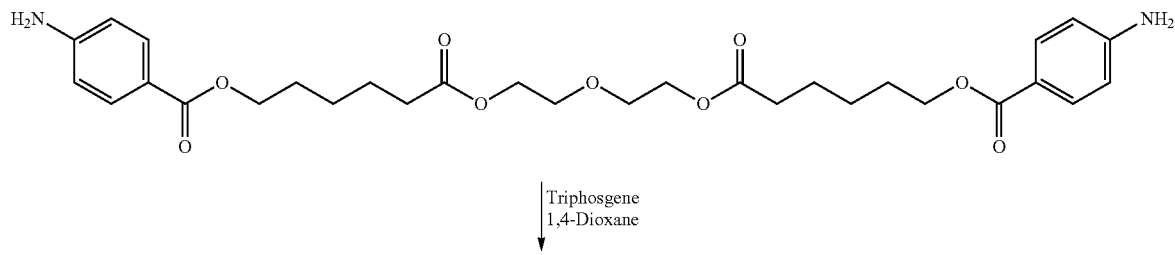

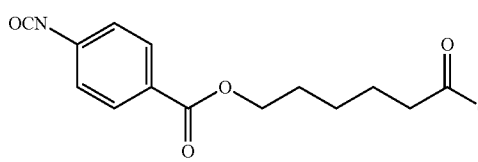 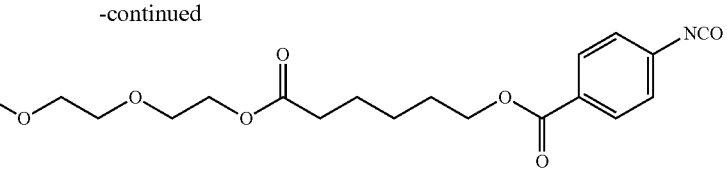

The above diamine (10 g) was dissolved in dry 1,4-dioxane (160 ml) under a nitrogen atmosphere and cooled below 10° C. A solution of triphosgene (8.8 g) in dry 1,4-dioxane (40 ml) was added. The mixture was heated slowly to 80° C. and maintained at that temperature for 2 hours. The condenser was then arranged for distillation and solvent was removed by distillation under atmospheric pressure until the volume of the reaction mixture had been reduced to approximately one third. Fresh dry 1,4-dioxane (300 ml) was added and the solvents were distilled off under vacuum. The residue was re-evaporated two times from dry 1,4-dioxane (600 ml) followed by dry toluene (50 ml). Charcoal (3 gram) was added and the solution was filtered hot. The toluene was distilled off under vacuum to yield pure diisocyanate (9 g) as light yellow syrup. The product was characterized by $^1$H NMR (CDCl$_3$) δ 1.48 (m, 2H, CH$_2$), 1.66 to 1.82 (m, 4H, 2×CH$_2$), 2.37 (t, 2H, CH$_2$), 3.68 (t, 2H, CH$_2$), 4.24 (t, 2H, CH$_2$), 4.34 (t, 2H, CH$_2$), 7.15 (d, 2H, Ar), 8.00 (d, 2H, Ar).

Similarly, substitution of thiophosgene for triphosgene provides the isothiocyanate analog. Also, preparation of the non-aromatic (reduced) analog is achieved by substitution of the corresponding cyclohexane analog, according to procedures known to those skilled in the art.

It will be understood that various modifications may be made to the embodiments disclosed herein. For example, the compositions in accordance with this disclosure can be blended with other biocompatible, bioabsorbable or non-bioabsorbable materials. Therefore, the above description should not be construed as limiting, but merely as an exemplification of preferred embodiments. Those skilled in the art may envision other modifications within the scope and spirit of the claims provided herein.

What is claimed is:

1. A diisocyanate or diamine compound having the structure of any of formulas (1), (2), (16) or (17):

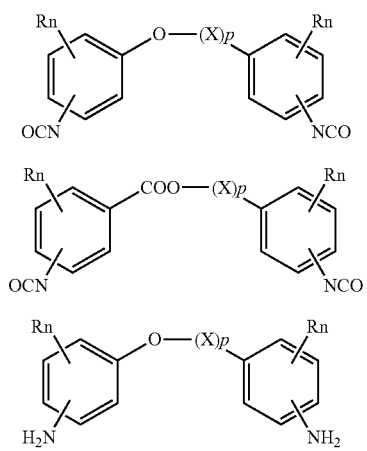

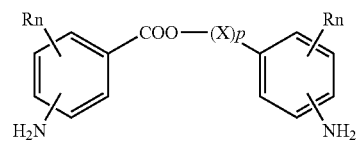

wherein each X represents a member independently selected from the group consisting of:
— CH$_2$COO— (glycolic acid moiety);
— CH(CH$_3$)COO— (lactic acid moiety);
— CH$_2$CH$_2$OCH$_2$COO— (dioxanone moiety);
— CH$_2$CH$_2$CH$_2$CH$_2$CH$_2$COO— (caprolactone moiety);
— (CH$_2$)$_y$COO— where y is one of the numbers 2, 3, 4 and 6-24 inclusive; and
— (CH$_2$CH$_2$O)$_{z'}$CH$_2$COO— where z' is an integer between 2 and 24, inclusive;
wherein Rn represents one or more substituents selected from the group consisting of hydrogen, alkoxy, phenoxy, benzyloxy, —CHO, halogen, carboxylic acid and nitro, which are attached directly to the aromatic ring or indirectly via an alkylene chain; and
wherein p is an integer between 1 and 4, inclusive.

2. The compound of claim 1, having the structure of formula (1) or (2).

3. The compound of claim 1, having the structure of formula (16) or (17).

4. An absorbable polymer comprising at least one compound of claim 1.

5. The absorbable polymer of claim 4, comprising a polymer selected from the group consisting of polyurethanes, polyamides, polyester urethanes and polyesteramides.

6. The absorbable polymer of claim 4, wherein each X is independently selected from the group consisting of:
— CH$_2$COO— (glycolic acid moiety),
— CH(CH$_3$)COO— (lactic acid moiety),
— CH$_2$CH$_2$OCH$_2$COO— (dioxanone moiety), and
— CH$_2$CH$_2$CH$_2$CH$_2$CH$_2$COO— (caprolactone moiety).

7. An article comprising a metal or polymeric substrate having thereon a coating comprising at least one polymer according to claim 4, wherein said article contacts mammalian tissue.

8. The article of claim 7, wherein said article is an implantable medical device.

9. A controlled drug delivery system comprising:
(1) one or more polymers according to claim 4, and
(2) one or more biologically or pharmacologically active agents.

10. The controlled drug delivery system of claim 9, wherein said one or more biologically or pharmacologically active agents are physically embedded or dispersed in a polymeric matrix comprising said one or more polymers.

11. A tissue scaffold comprising one or more polymers according to claim 4, wherein said tissue scaffold has a porous structure for the attachment and proliferation of cells, either in vitro or in vivo.

12. A nutritional supplement comprising at least one polymer according to claim 4.

13. The polymer according to claim 4, wherein said polymer is further polymerized on at least one end with polyesters of at least one lactone monomer selected from the group consisting of glycolide, lactide, p-dioxanone, trimethylene carbonate and caprolactone.

14. An article comprising a metal or polymeric substrate wherein said article is used in
   (a) medicinal, medical device, therapeutic, consumer product, cosmetic or tissue engineering applications, or
   (b) wound healing and/or controlled drug delivery, and comprises a foam, or
   (c) sutures, bone hemostats, bone fillers, bone void fillers, bone cements, tissue adhesives, tissue sealants, adhesion prevention barriers, meshes, or filters, or
   (d) stents, medical device coatings, pharmaceutical drug formulations, cosmetic packaging, pharmaceutical packaging, apparel, infusion devices, blood collection devices, tubes, skin care products or transdermal drug delivery materials, and
wherein said article comprises at least one polymer according to claim 5.

15. The article of claim 14, wherein said foam comprises a reticulated foam.

16. The polymer of claim 4, containing at least one repeating unit of at least one of the compounds selected from formula (1) or (2).

17. The polymer of claim 4, containing at least one repeating unit of at least one of the compounds selected from formula (16) or (17).

18. A diisocyanate or diamine compound selected from the group consisting of the structures having formulas (I) to (IV), (IX) to (XVI), and (XXIX) to (XXXII):

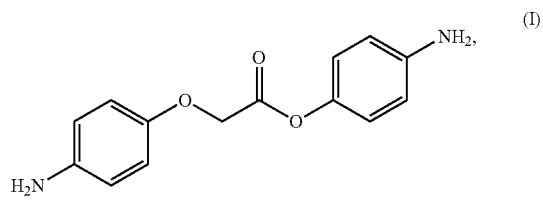
(I)

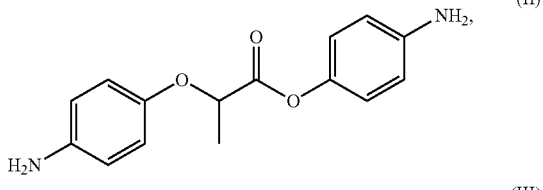
(II)

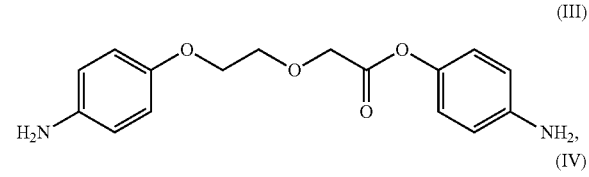
(III)

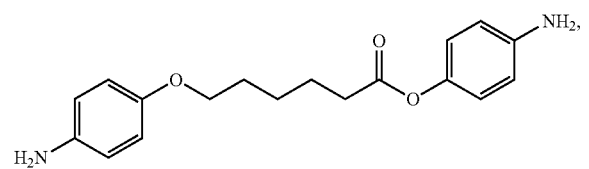
(IV)

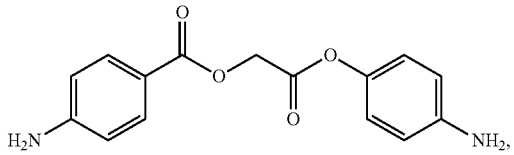
(IX)

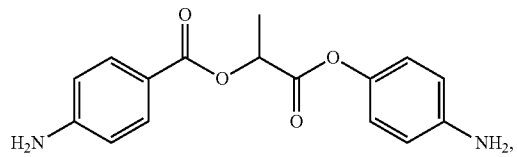
(X)

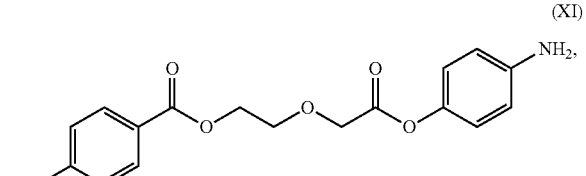
(XI)

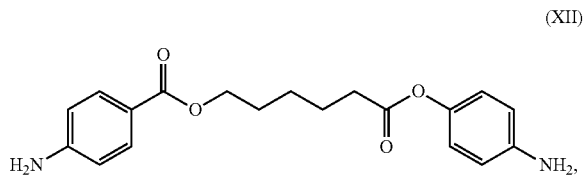
(XII)

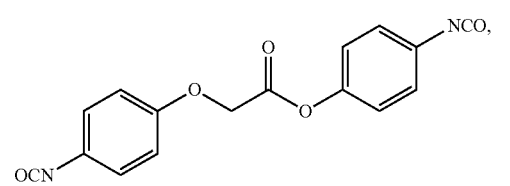
(XIII)

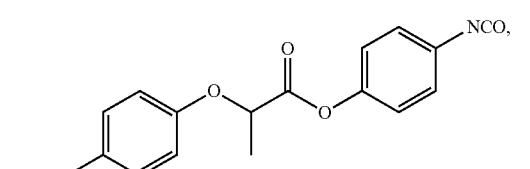
(XVI)

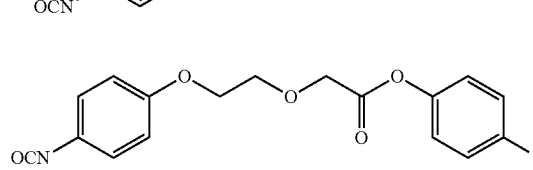
(XV)

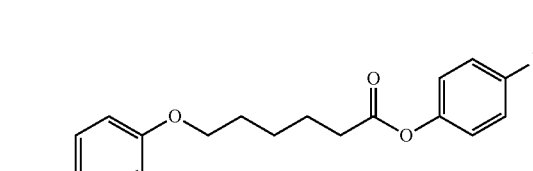
(XVI)

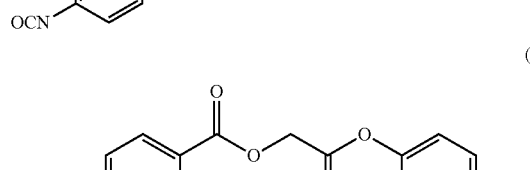
(XXIX)

-continued
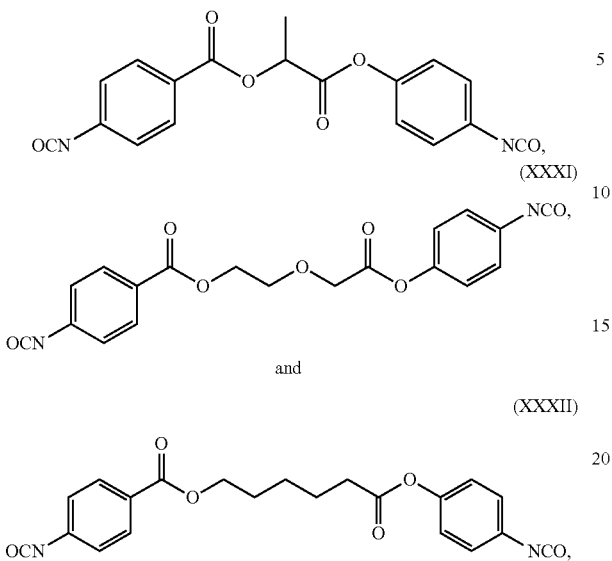
19. A polymer comprising at least one repeating unit of at least one compound of claim 18.
20. A composition comprising the polymer of claim 19. amendments have been made; however, status identifiers have been updated.
* * * * *

UNITED STATES PATENT AND TRADEMARK OFFICE
CERTIFICATE OF CORRECTION

| | | |
|---|---|---|
| PATENT NO. | : 8,901,347 B1 | Page 1 of 1 |
| APPLICATION NO. | : 13/275902 | |
| DATED | : December 2, 2014 | |
| INVENTOR(S) | : Rao S Bezwada | |

It is certified that error appears in the above-identified patent and that said Letters Patent is hereby corrected as shown below:

In the Claims

Column 68, line 40, replace:

"(XVI)"

with

"(XIV)".

Column 69, lines 29-30, delete:

"amendments have been made; however, status identifiers have been updated.".

Signed and Sealed this
Tenth Day of March, 2015

Michelle K. Lee
*Deputy Director of the United States Patent and Trademark Office*